(12) United States Patent
Yaku et al.

(10) Patent No.: US 8,232,054 B2
(45) Date of Patent: *Jul. 31, 2012

(54) METHOD FOR DETECTING G-QUADRUPLEX, METHOD FOR DETECTING G-QUADRUPLEX-FORMING DNA AND METHOD FOR DETERMINING TELOMERASE ACTIVITY

(75) Inventors: Hidenobu Yaku, Osaka (JP); Daisuke Miyoshi, Hyogo (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/335,498

(22) Filed: Dec. 22, 2011

(65) Prior Publication Data

US 2012/0094282 A1    Apr. 19, 2012

Related U.S. Application Data

(63) Continuation of application No. 12/649,948, filed on Dec. 30, 2009, now Pat. No. 8,119,347, which is a continuation of application No. PCT/JP2009/002304, filed on May 26, 2009.

(30) Foreign Application Priority Data

May 27, 2008    (JP) .................................. 2008-137574

(51) Int. Cl.
*C12Q 1/68*    (2006.01)
(52) U.S. Cl. ........................................................ 435/6.1
(58) Field of Classification Search .......................... None
See application file for complete search history.

(56) References Cited

U.S. PATENT DOCUMENTS 6,087,493 A    7/2000    Wheelhouse et al.
6,492,117 B1    12/2002    Choo et al.

FOREIGN PATENT DOCUMENTS

| WO | WO 98/33503 | 8/1998 |
| WO | WO 2004/072027 A2 | 8/2004 |
| WO | WO 2007/090343 A1 | 8/2007 |

OTHER PUBLICATIONS

Dixon, I.M., et al., "A G-Quadruplex Ligand with 10000-Fold Selectivity over Duplex DNA", Journal of the American Chemical Society, 2007, pp. 1502-1503, vol. 129, American Chemical Society, Washington DC USA.
Gonçalves, D., et al., "Tetramethylpyridiniumporphyrazines—a new class of G-quadruplex inducing and stablishing ligands", Chem. Commun., 2006, pp. 4685-4687, The Royal Society of Chemistry.
Zhang, L., et al., "Synthesis and evaluation of cationic phthalocyanine derivatives as potential inhibitors of telomerase", Bioorganic & Medicinal Chemistry, 2008, pp. 303-312, vol. 16, Elsevier.

*Primary Examiner* — Christopher M. Babic
(74) *Attorney, Agent, or Firm* — McDermott Will & Emery LLP

(57) ABSTRACT

A method is provided for specifically detecting a G-quadruplex, and the like. The method is characterized by including the steps of preparing a solution including an anionic planar phthalocyanine and mixing the solution with a sample solution to obtain a liquid mixture. The solution includes an anionic planar phthalocyanine. The method also includes a step of measuring the absorbance at 640 to 740 nm of the obtained liquid mixture.

3 Claims, 36 Drawing Sheets

[Fig. 1]
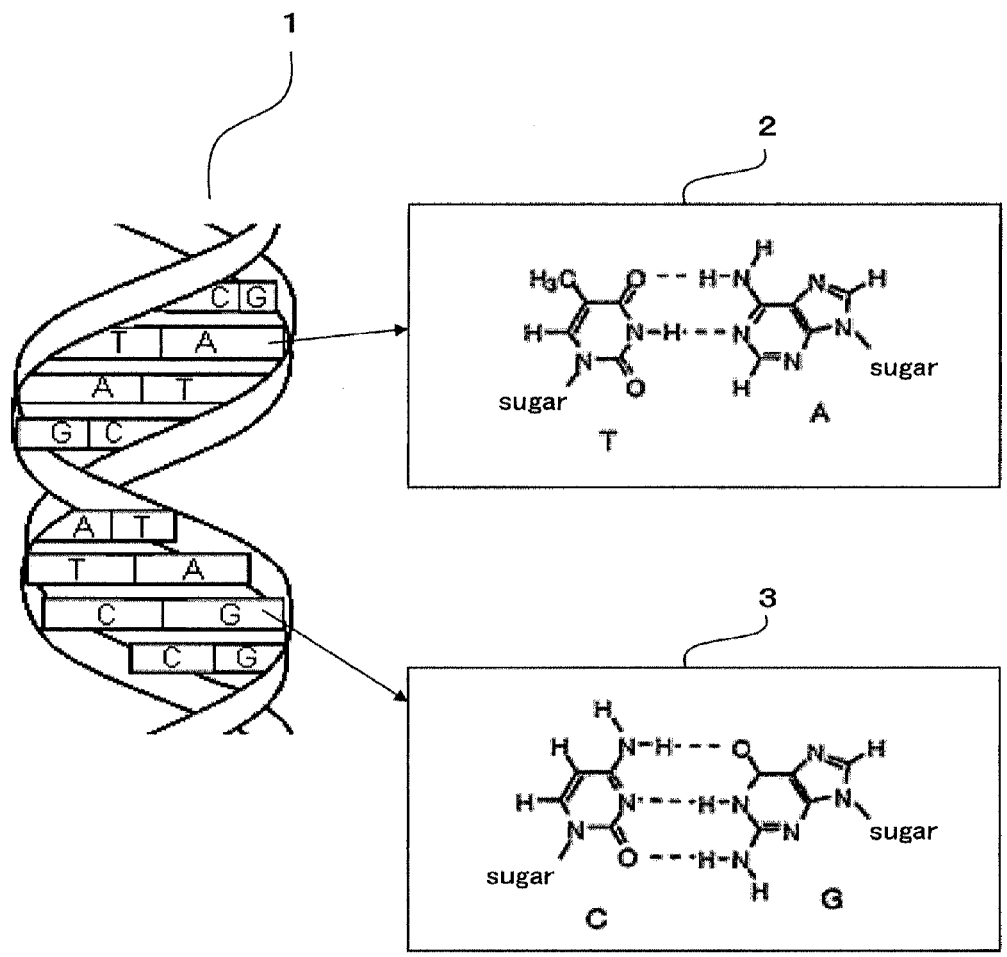
Prior Art

[Fig. 2]
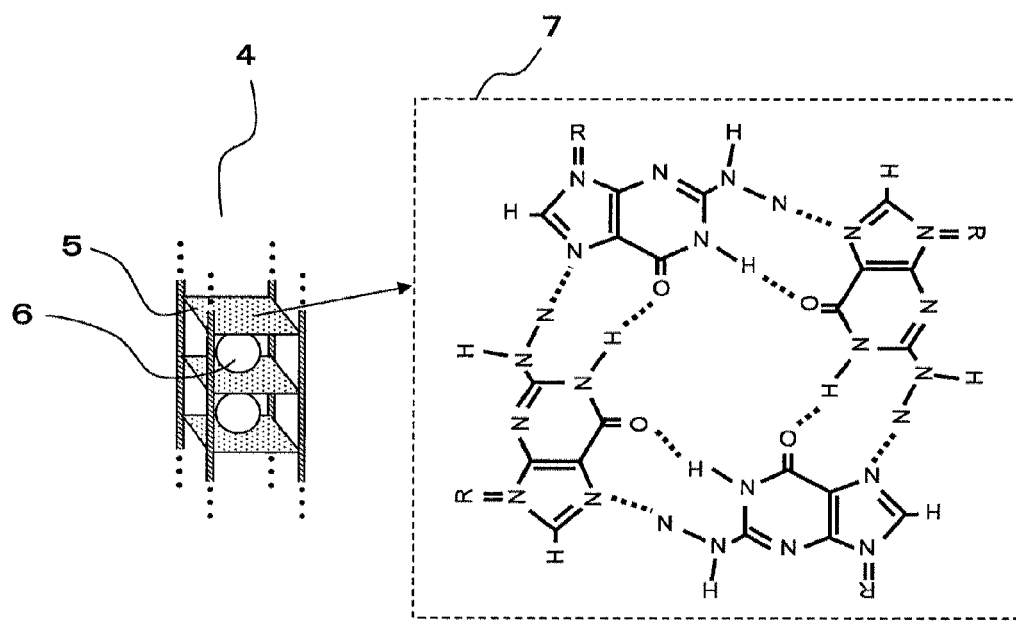
Prior Art

[Fig. 3]
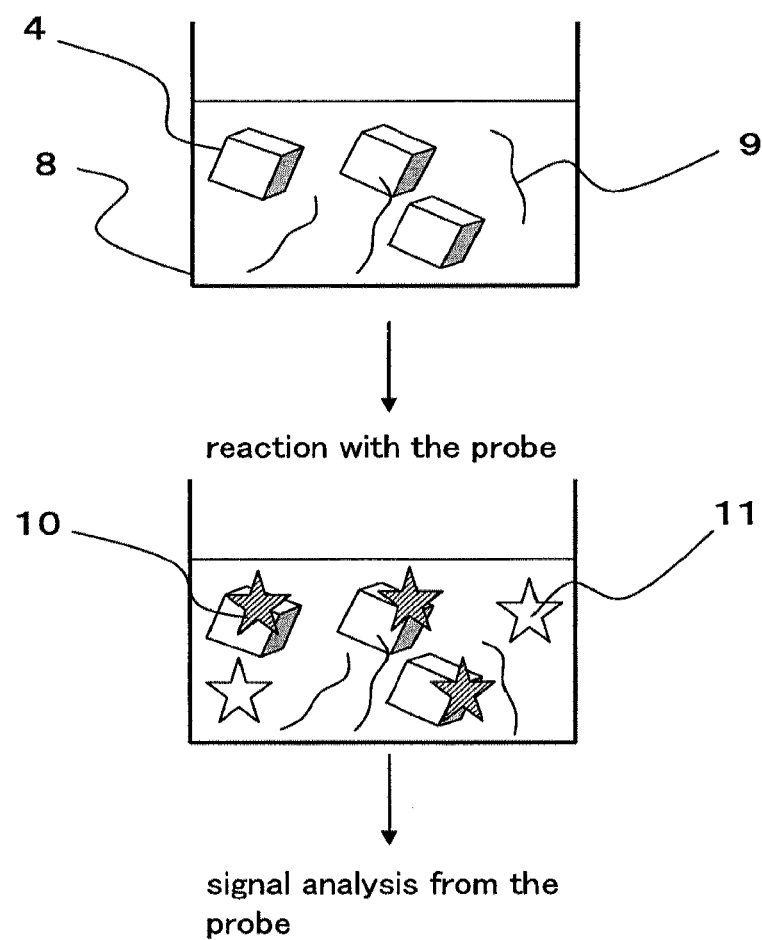

[Fig. 4]
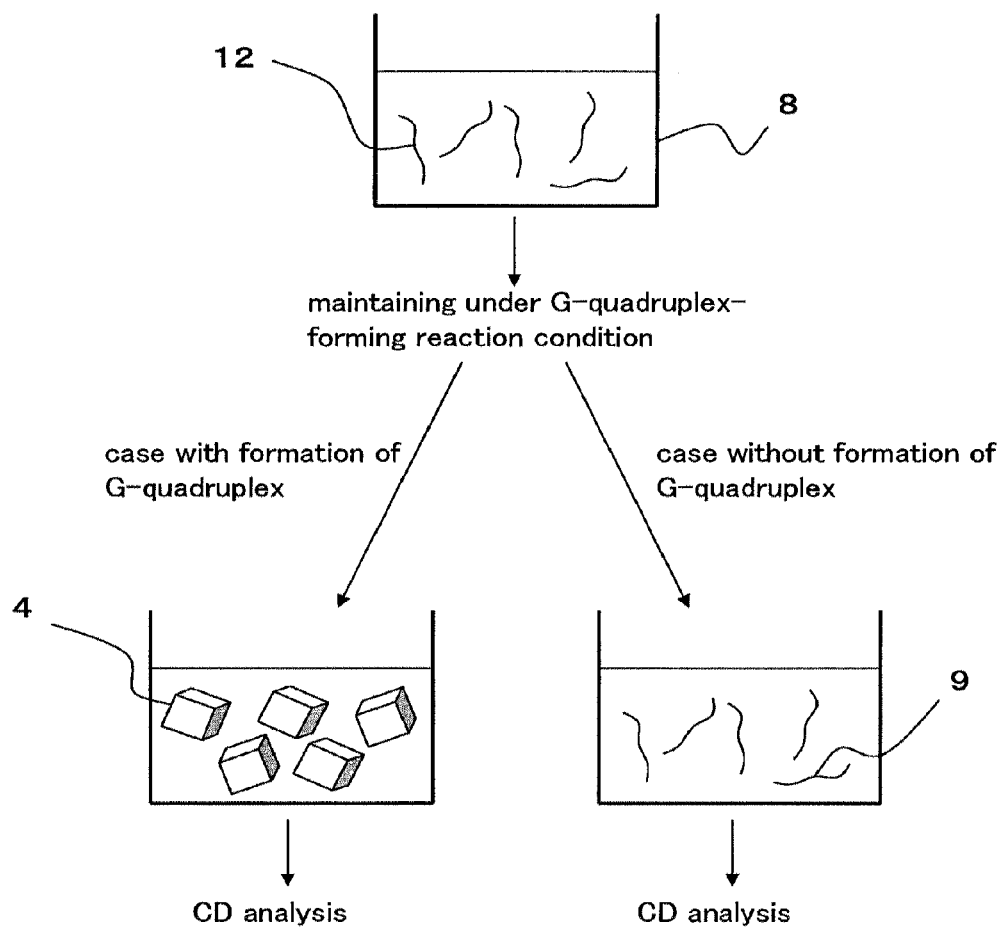

[Fig. 5]
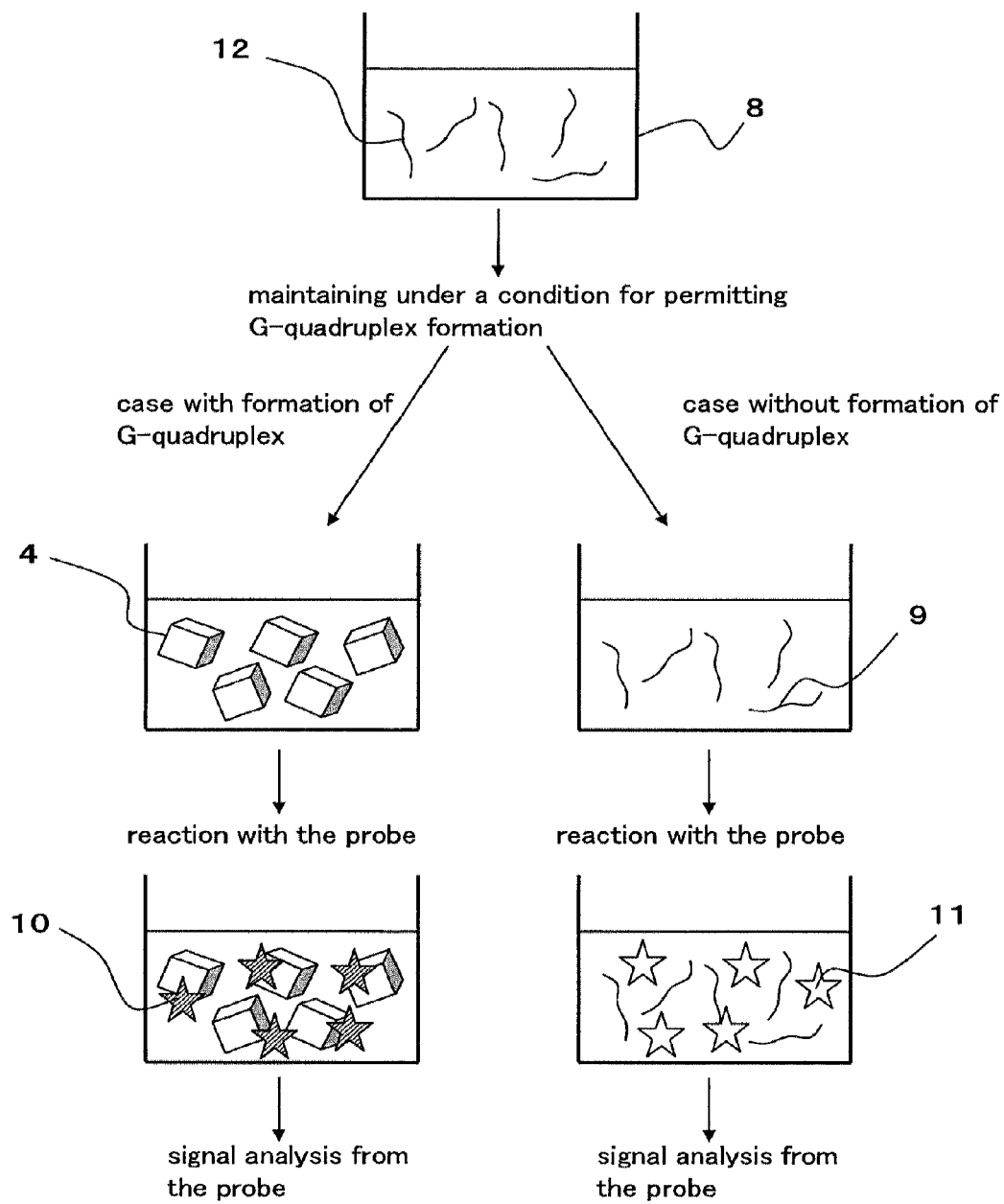

[Fig. 6]
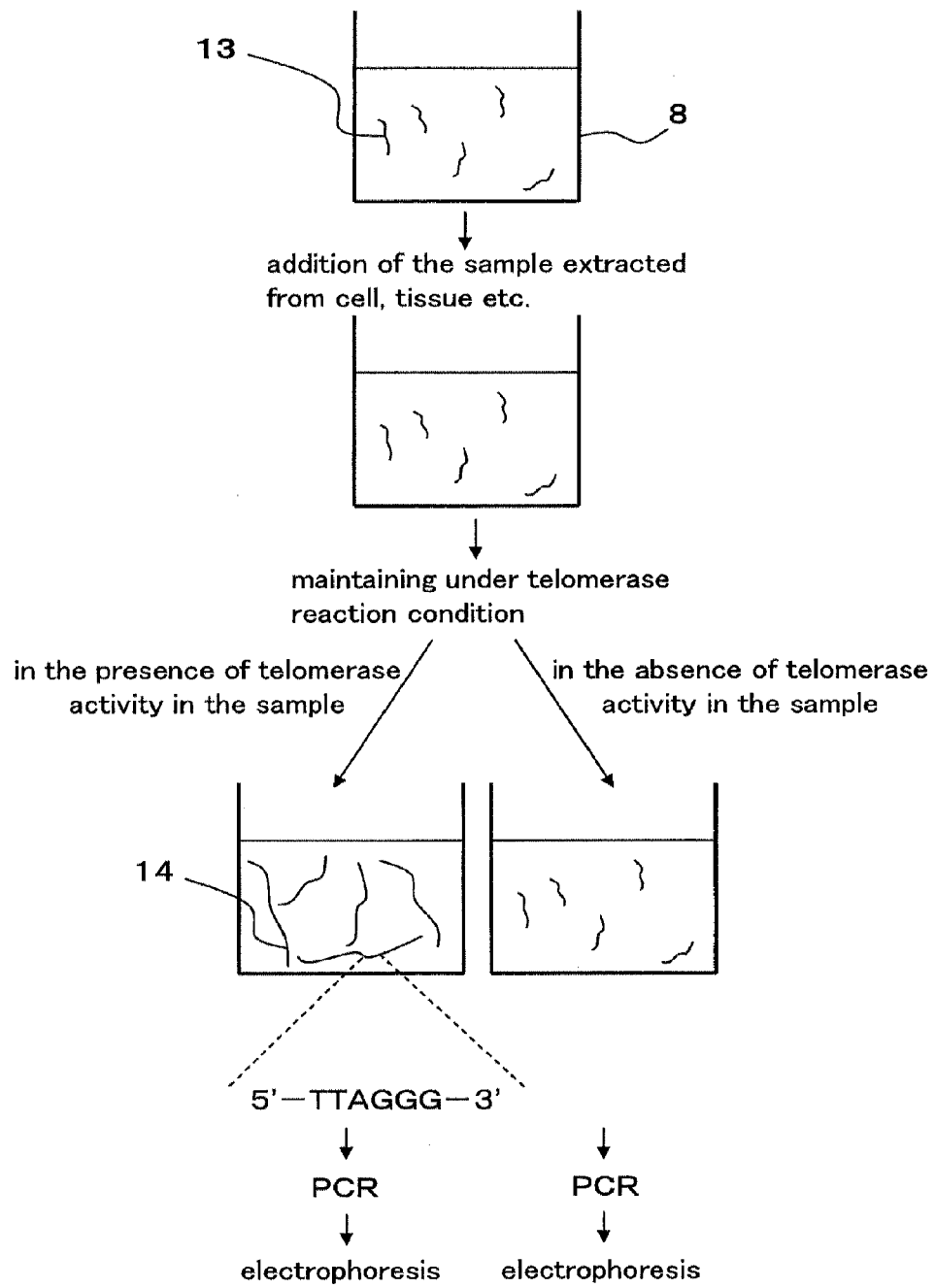
Prior Art

[Fig. 7]
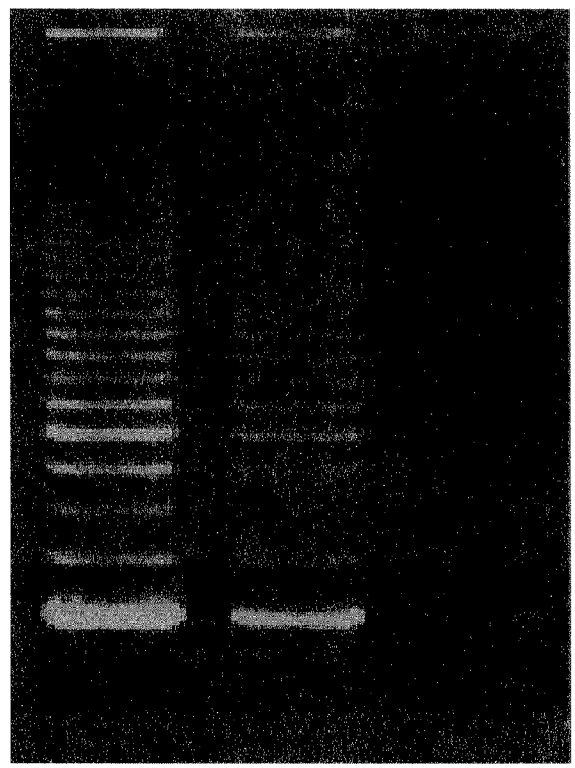
telomerase activity:
lane 1>lane 2>lane 3
Prior Art

[Fig. 8]
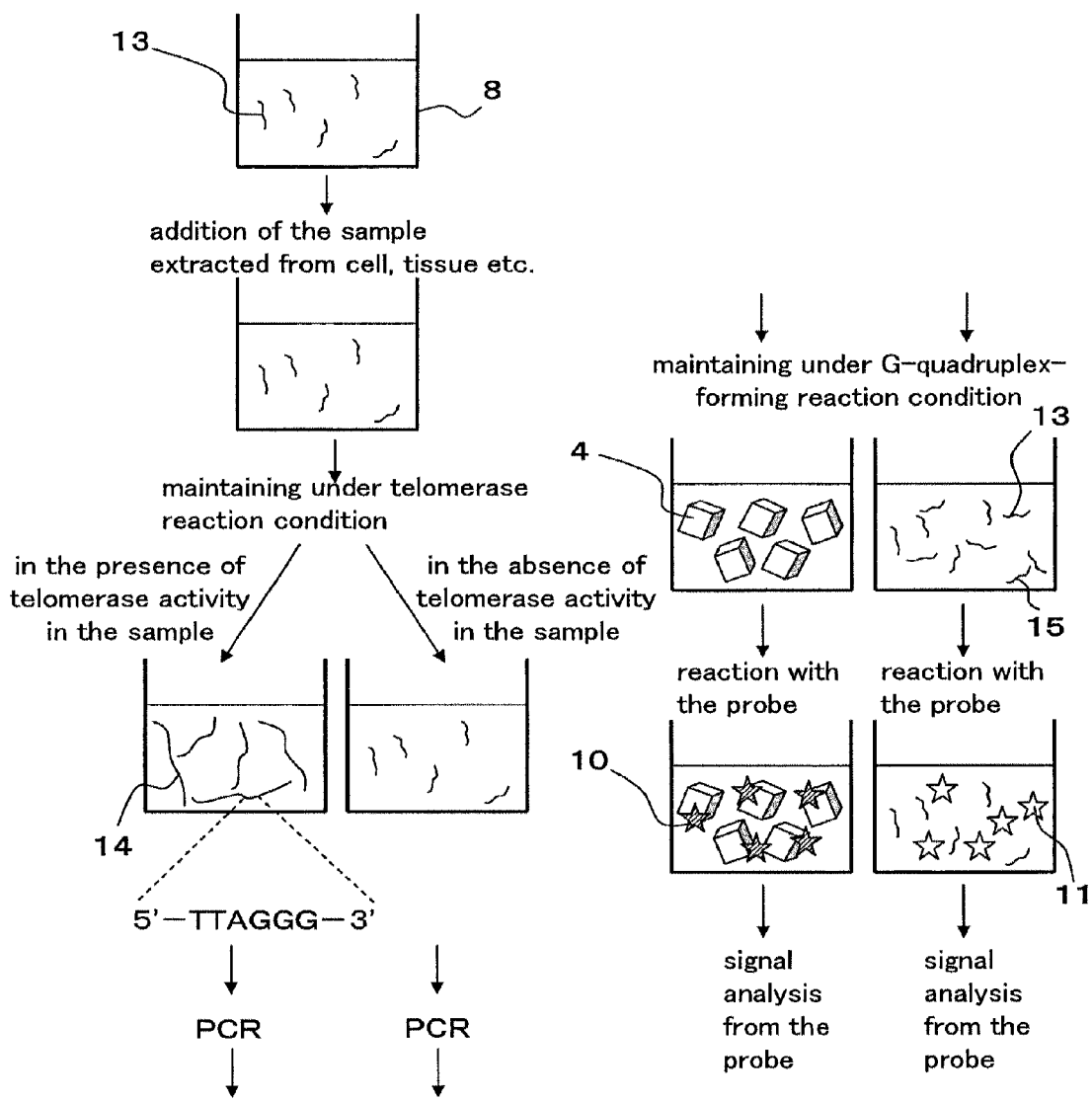

[Fig. 9]
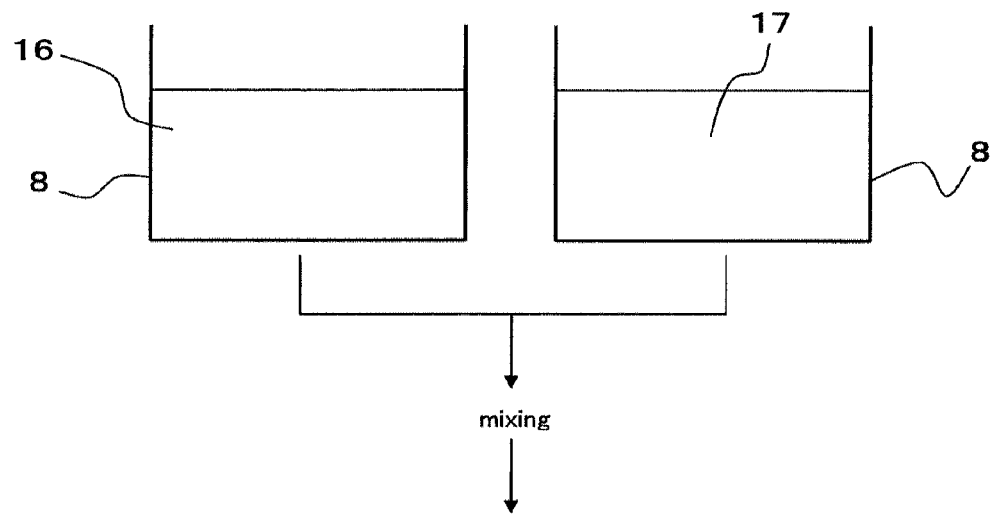
Measurement of absorbance value at the absorption peak dependent on the G-quadruplex in the range of 640 to 740 nm

[Fig. 10]
(A)
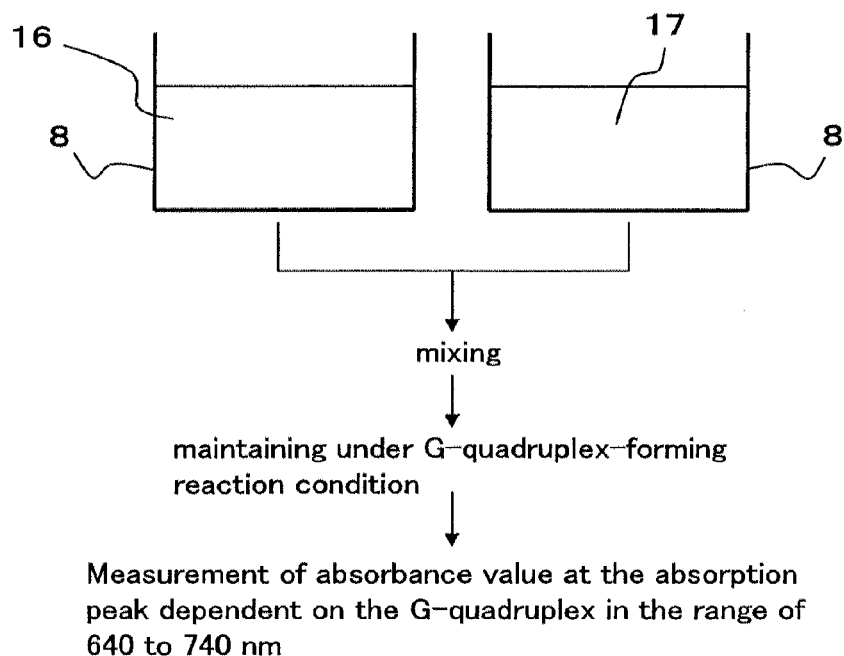
mixing
maintaining under G-quadruplex-forming reaction condition
Measurement of absorbance value at the absorption peak dependent on the G-quadruplex in the range of 640 to 740 nm
(B)
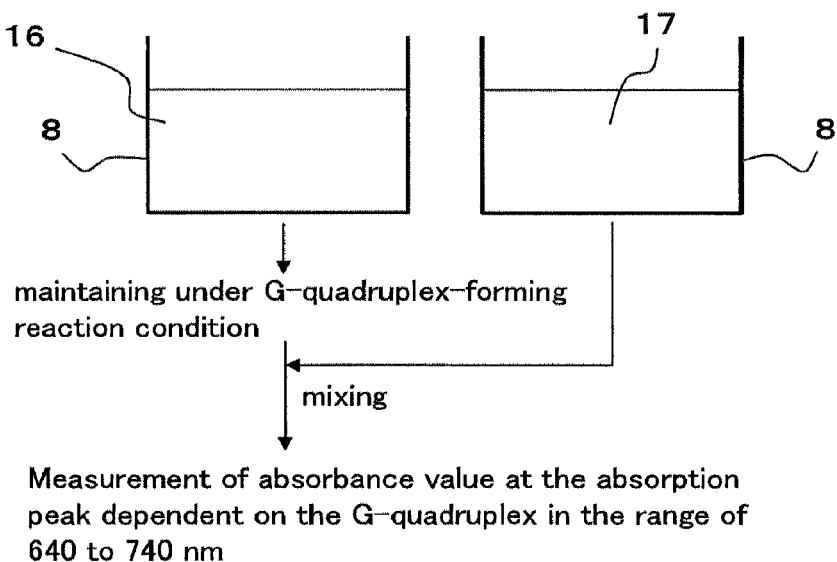
maintaining under G-quadruplex-forming reaction condition
mixing
Measurement of absorbance value at the absorption peak dependent on the G-quadruplex in the range of 640 to 740 nm

[Fig. 11]
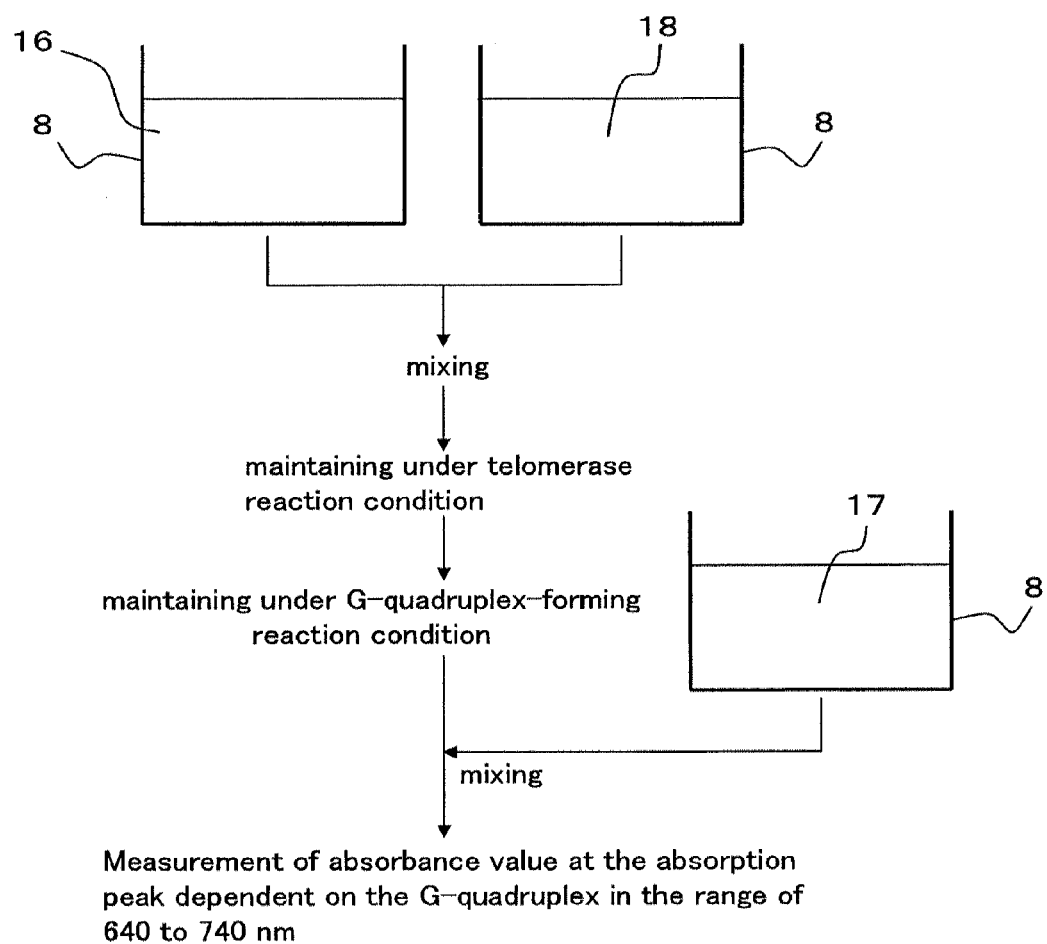

[Fig. 12]
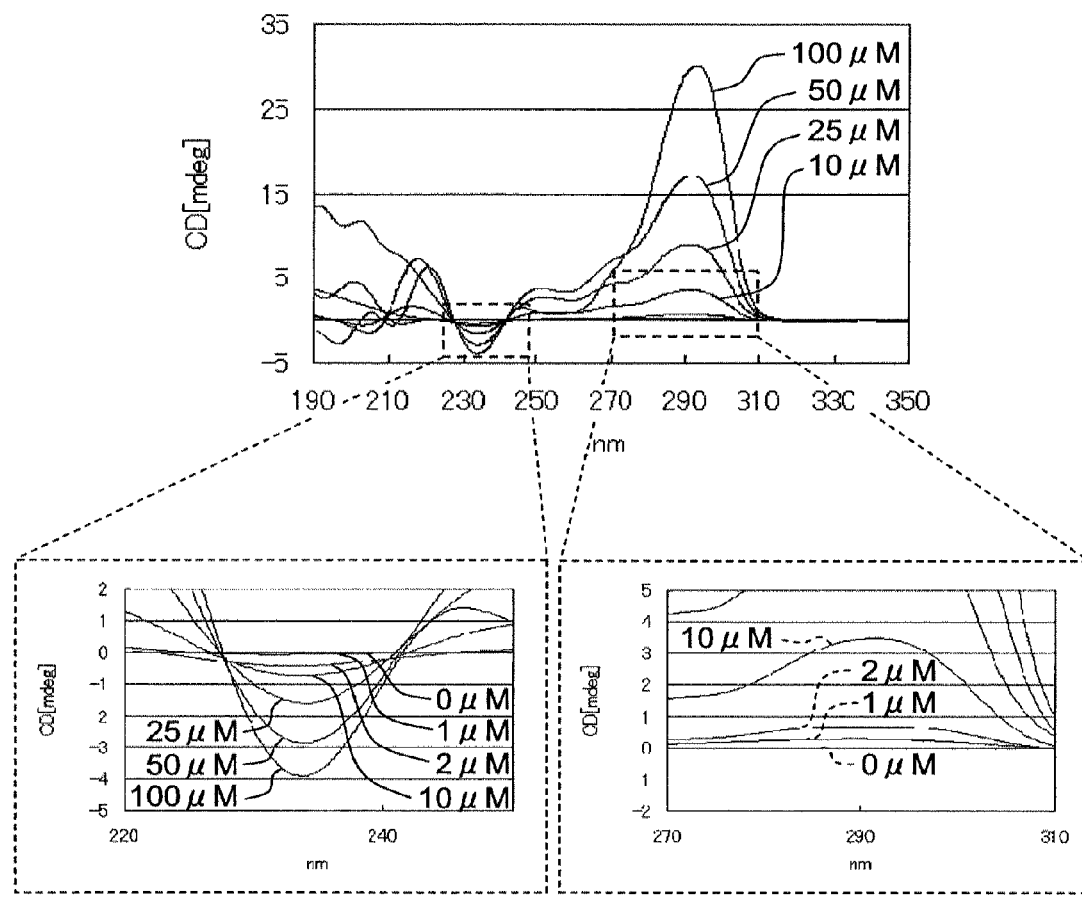

[Fig. 13]
(A)
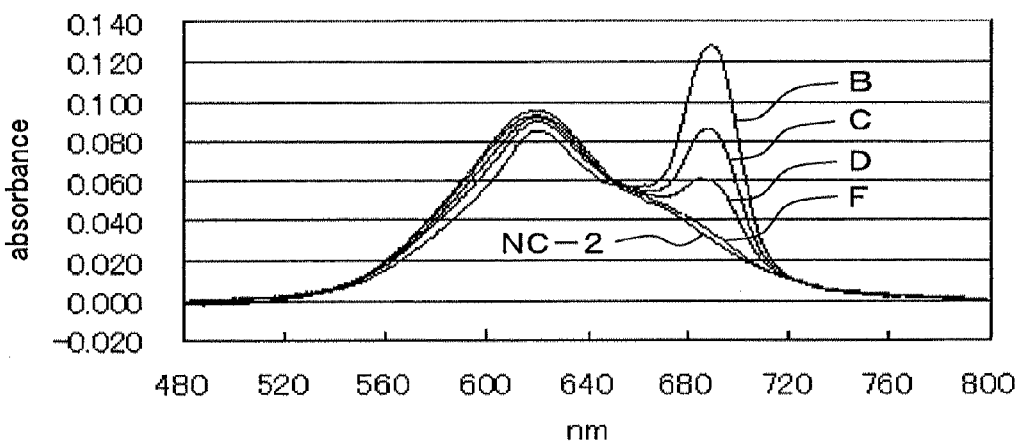
(B)
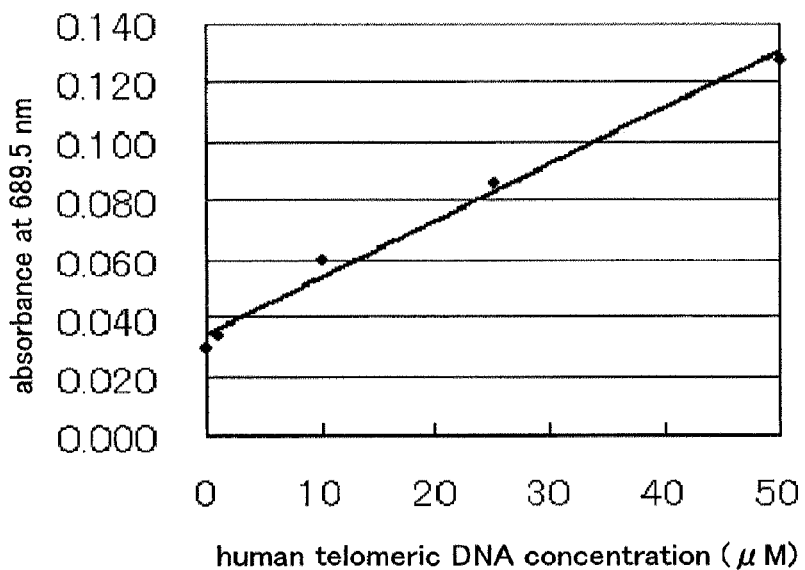

[Fig. 14]
(A)
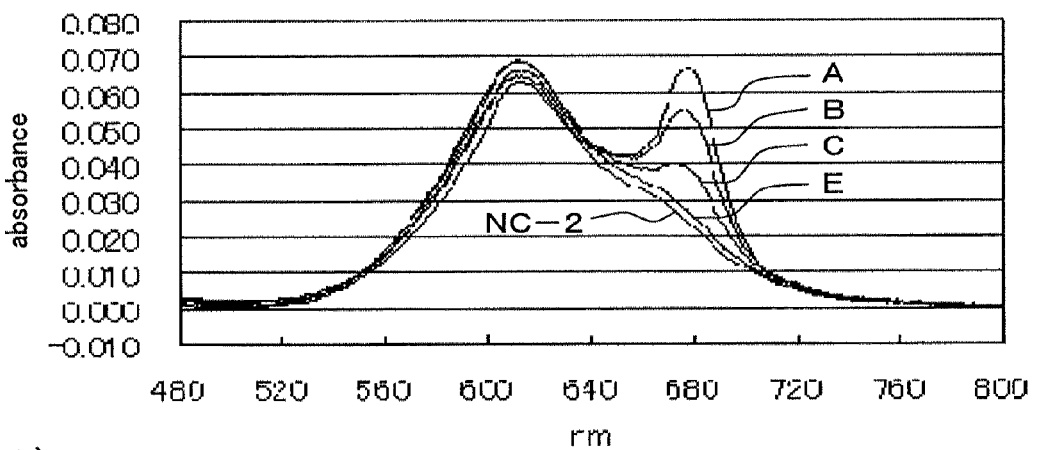
(B)
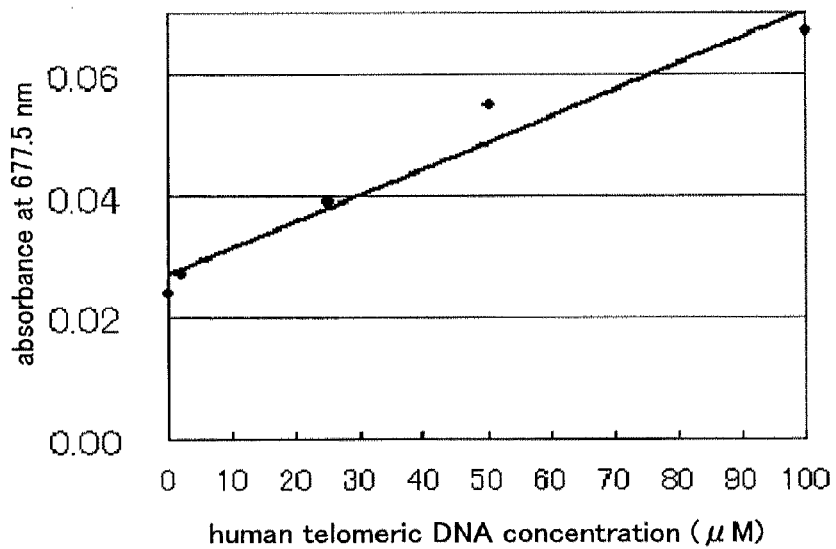

[Fig. 15]
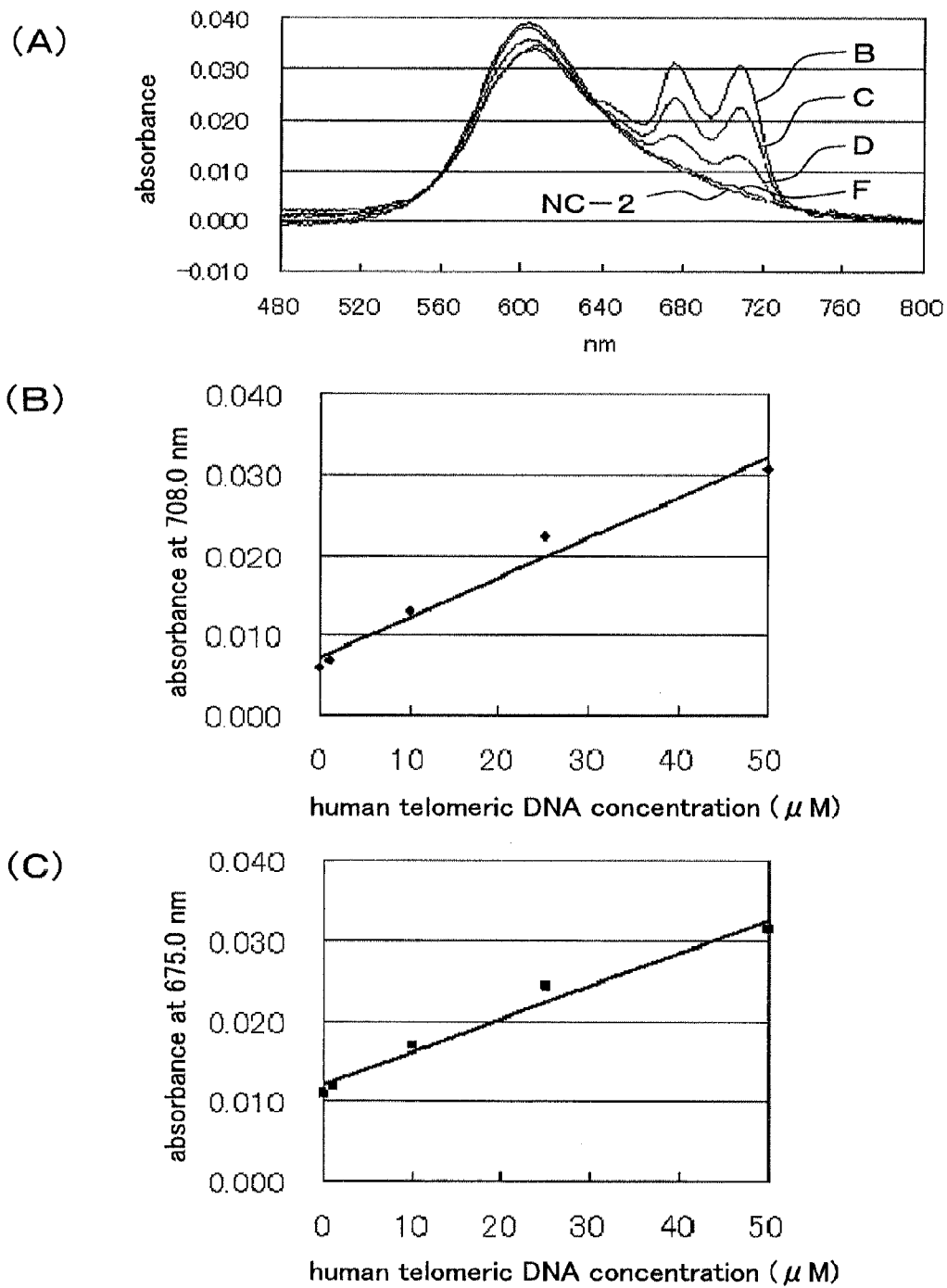

[Fig. 16]
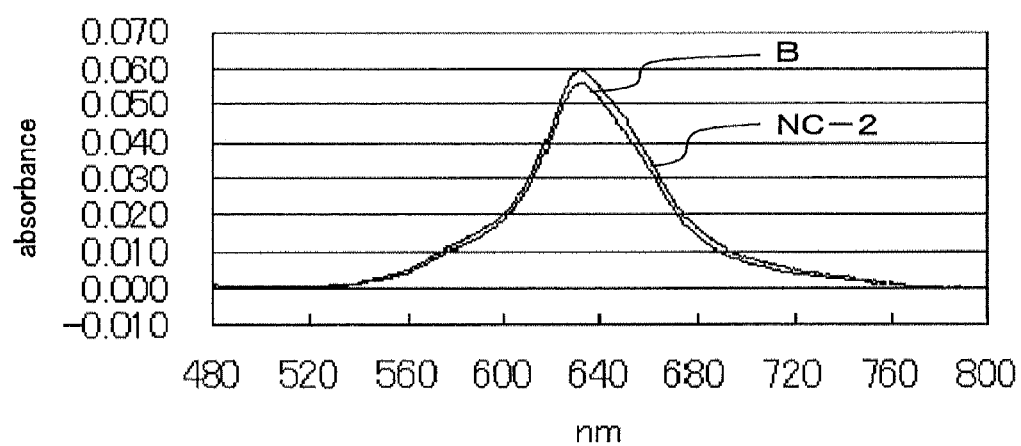

[Fig. 17]
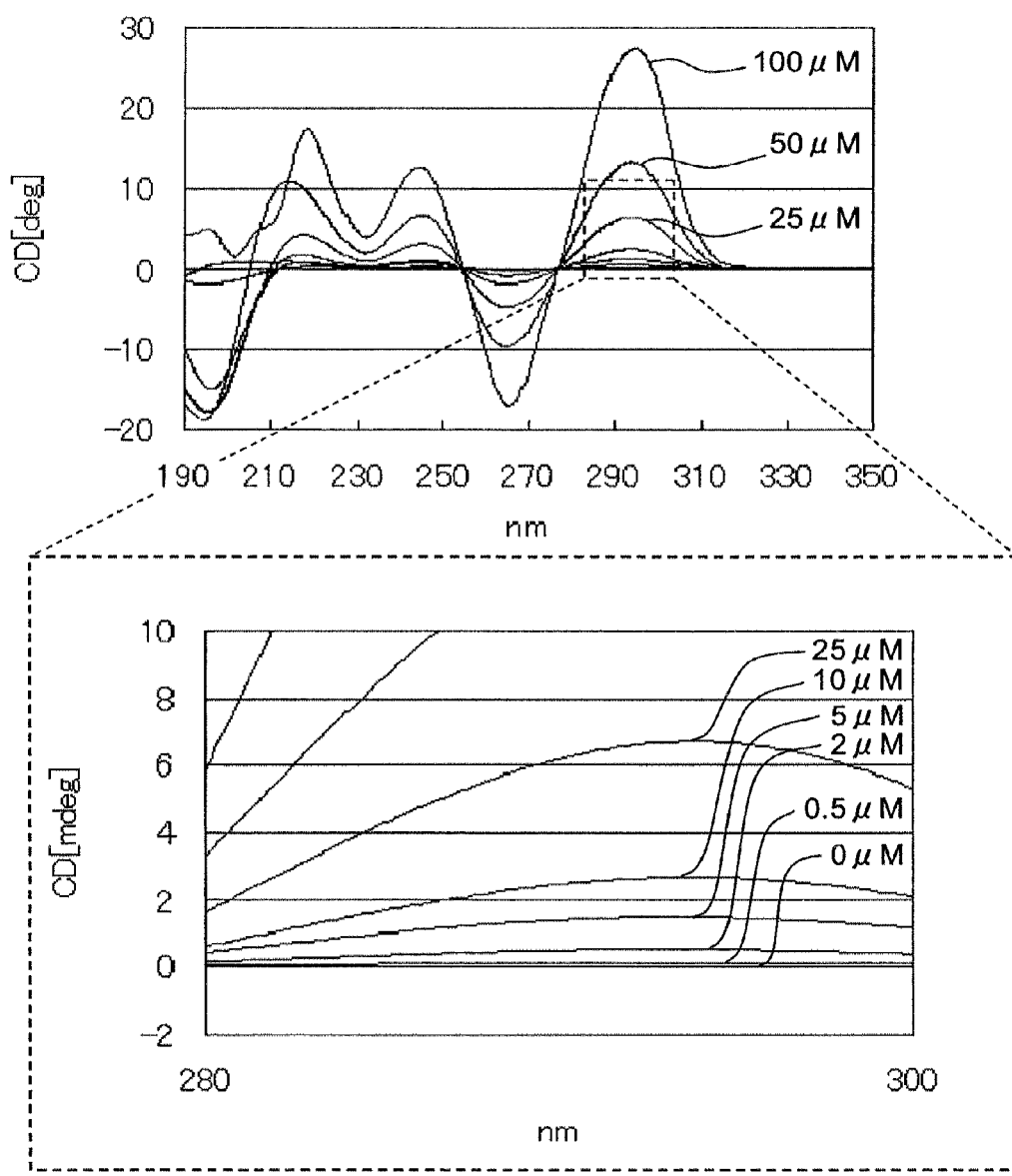

[Fig. 18]
(A)
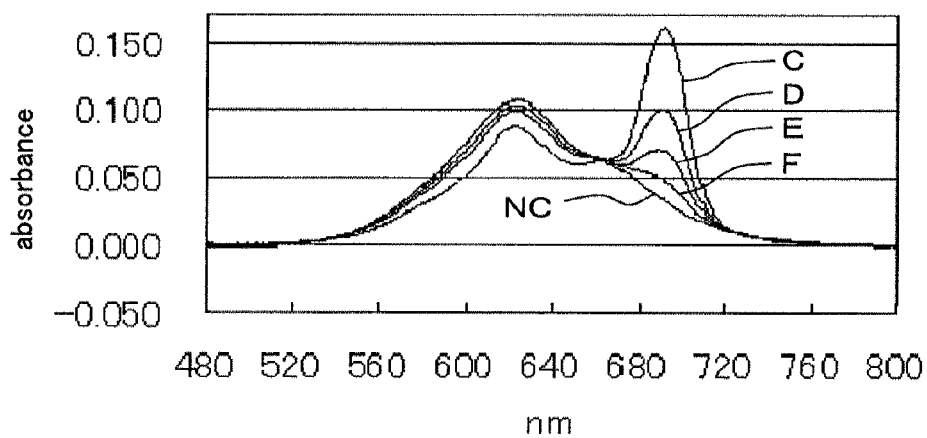
(B)
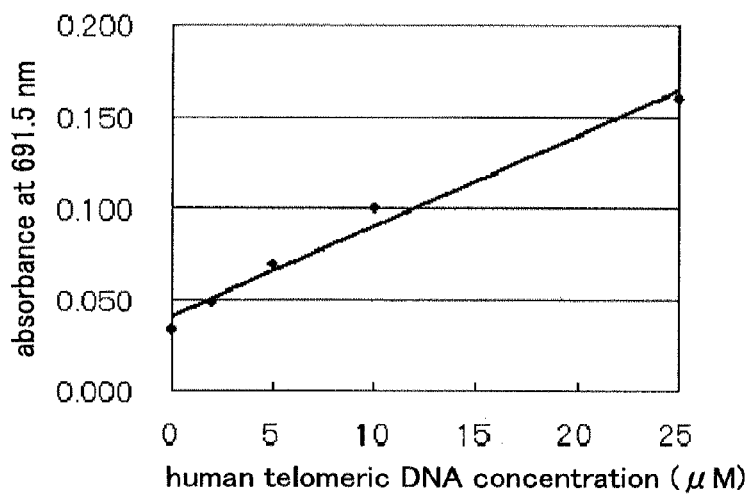

[Fig. 19]
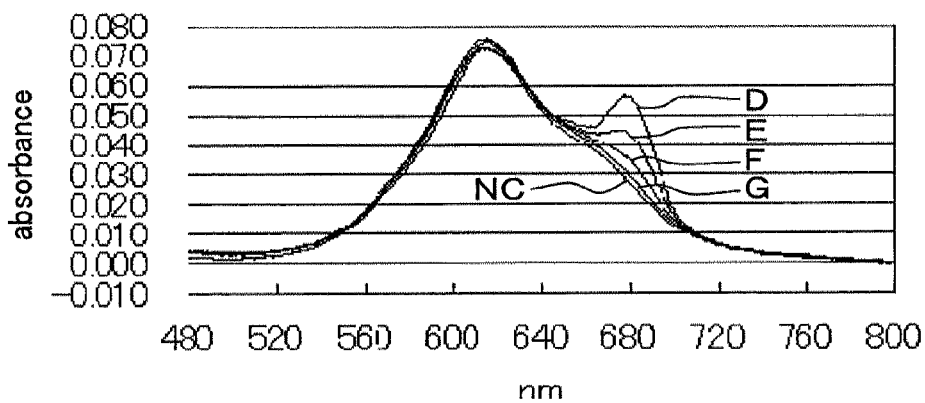
(A)
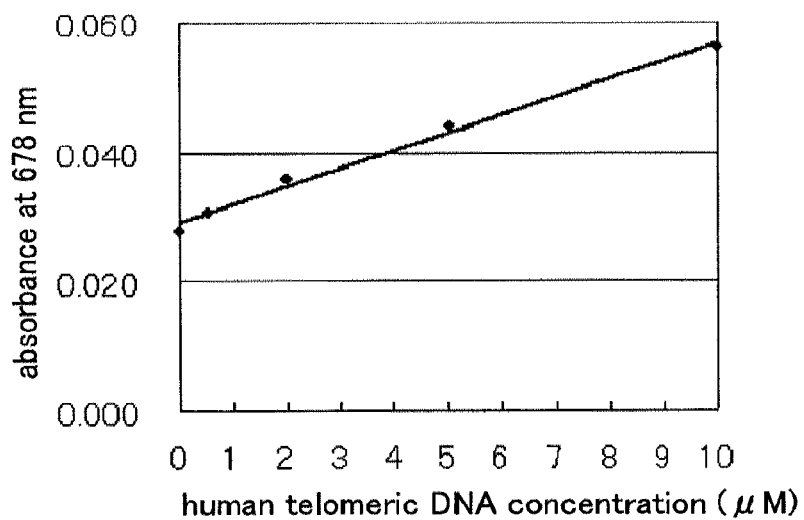
(B)

[Fig. 20]
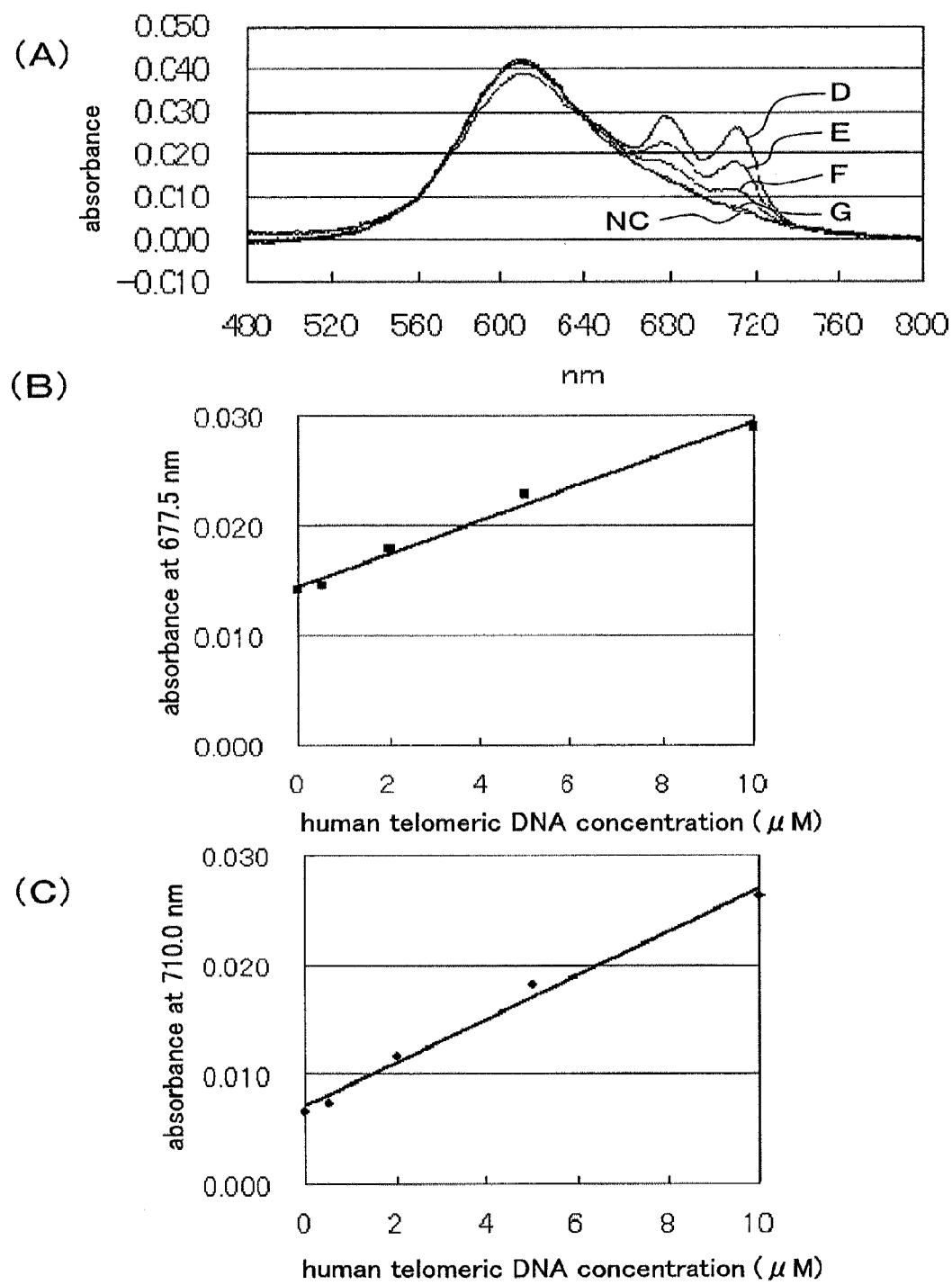

[Fig. 21]
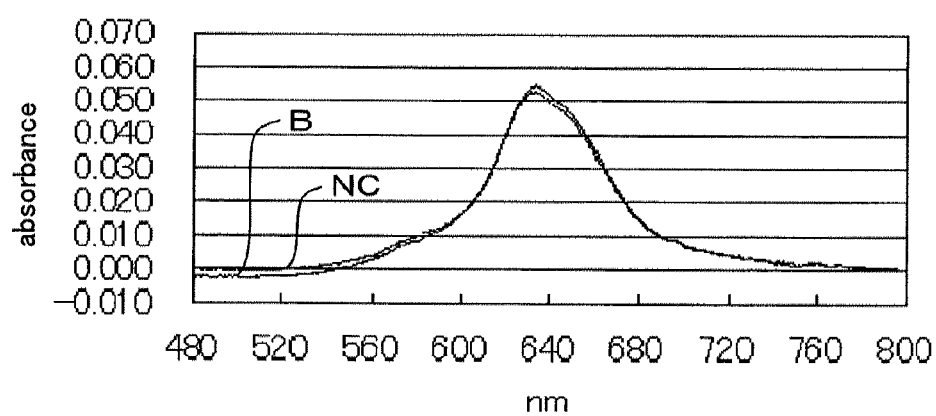

[Fig. 22]
(A)
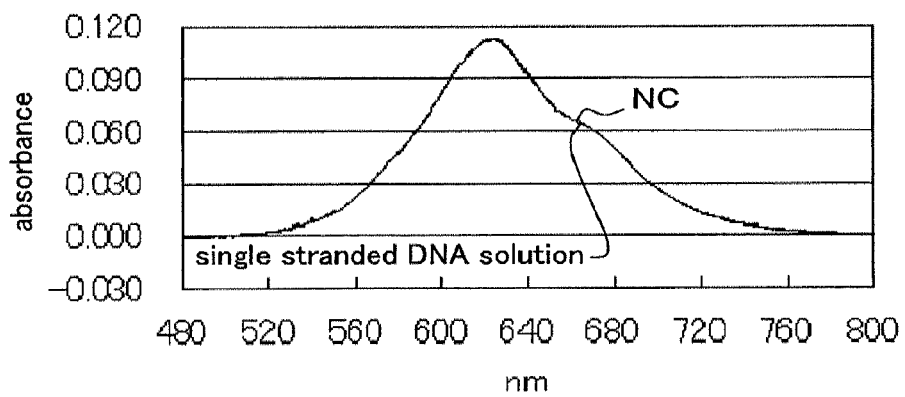
(B)
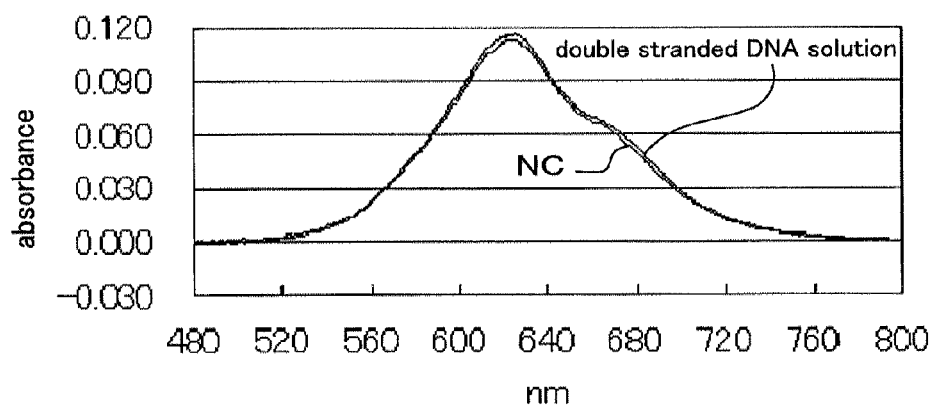

[Fig. 23]
(A)
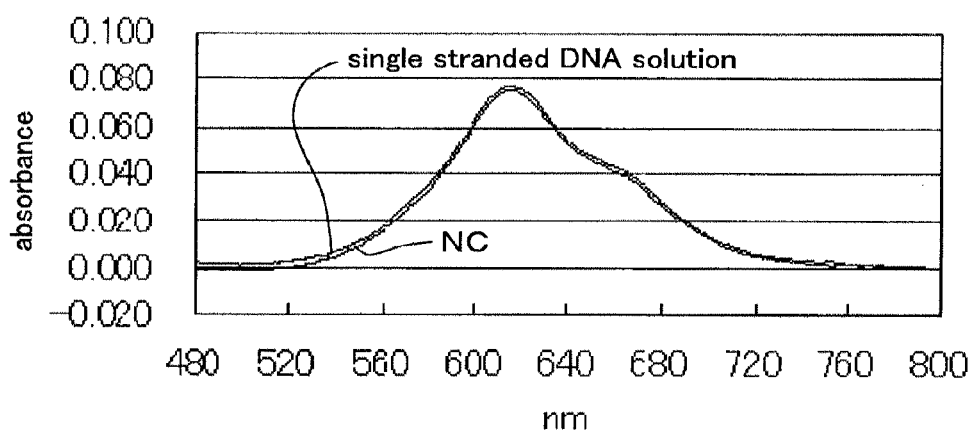
(B)
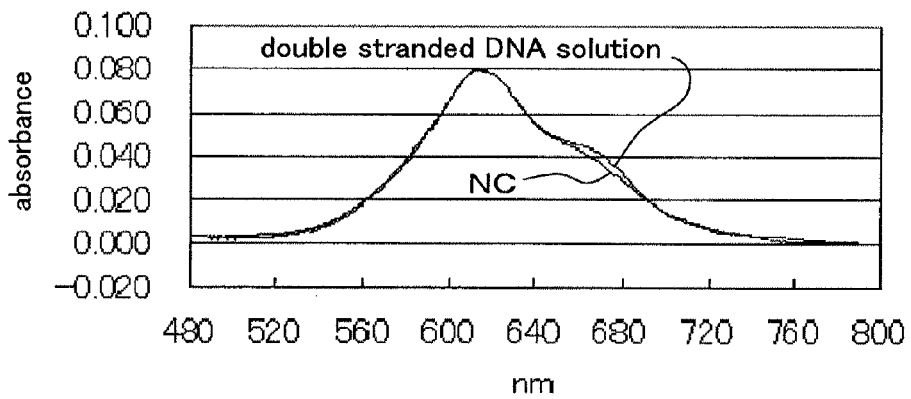

[Fig. 24]
(A)
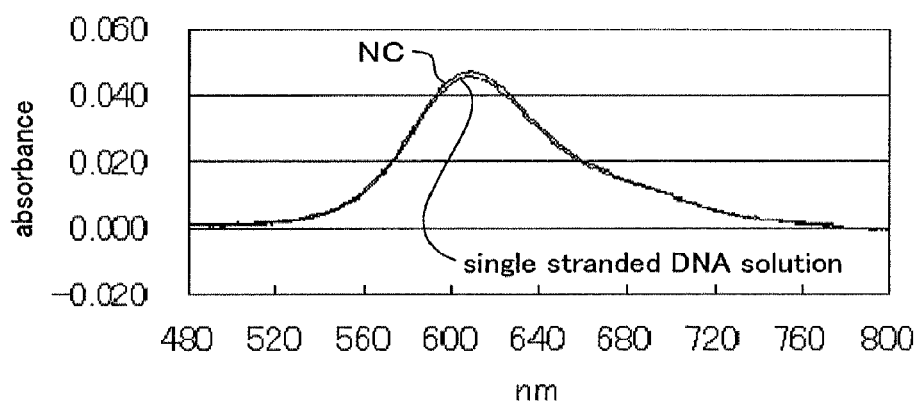
(B)
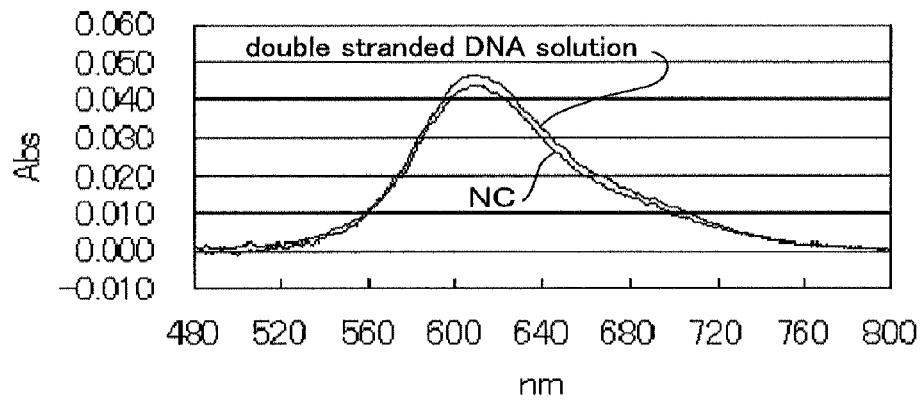

[Fig. 25]
(A)
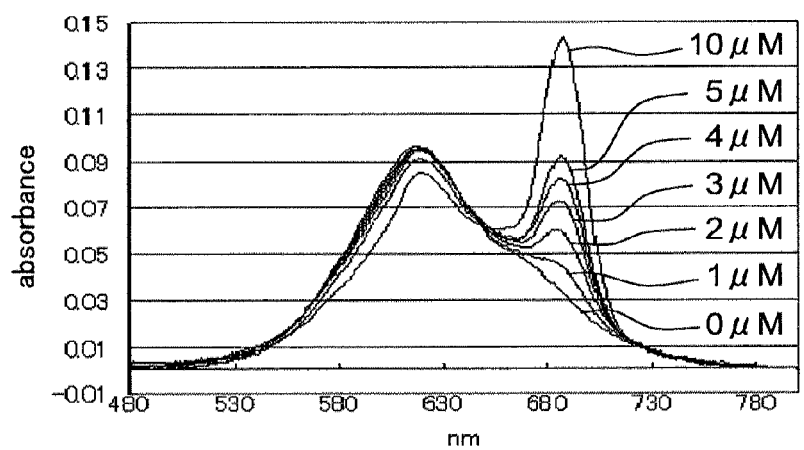
(B)
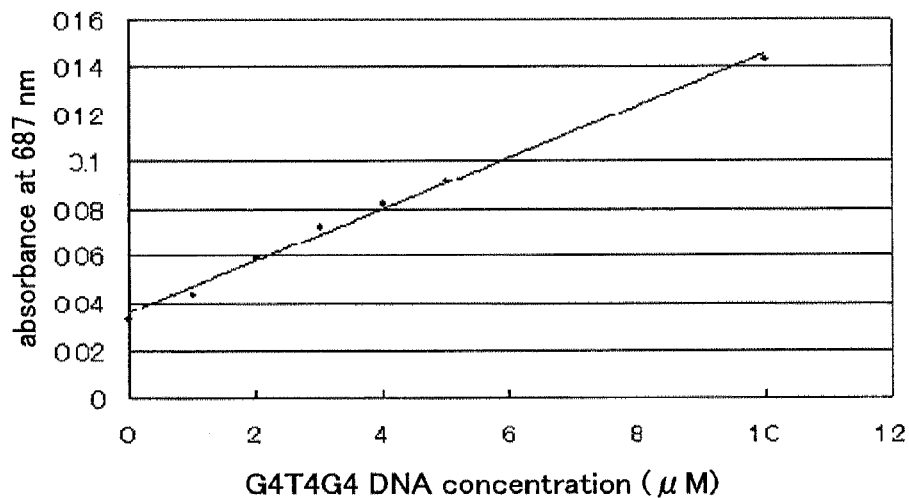

[Fig. 26]
(A)
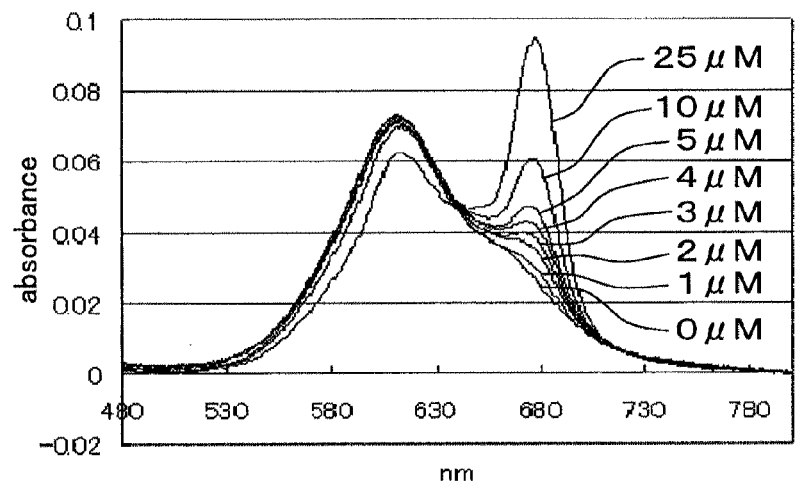
(B)
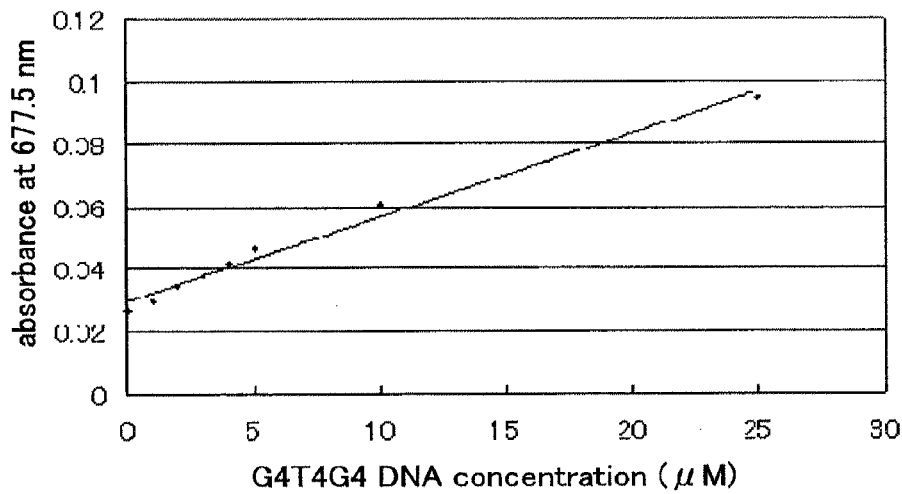

[Fig. 27]
(A)
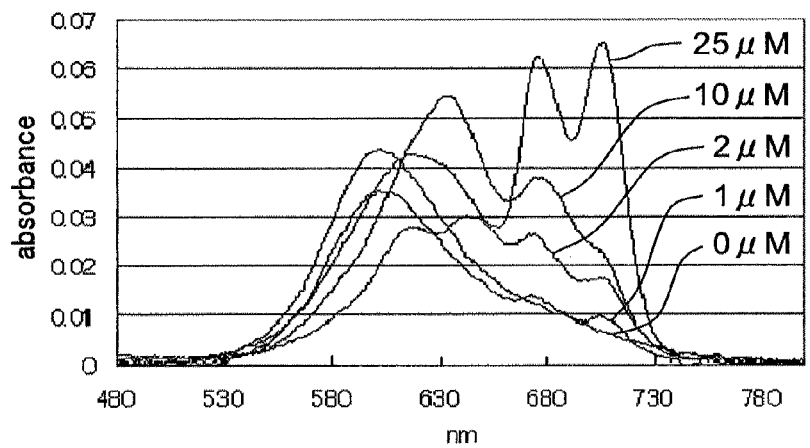
(B)
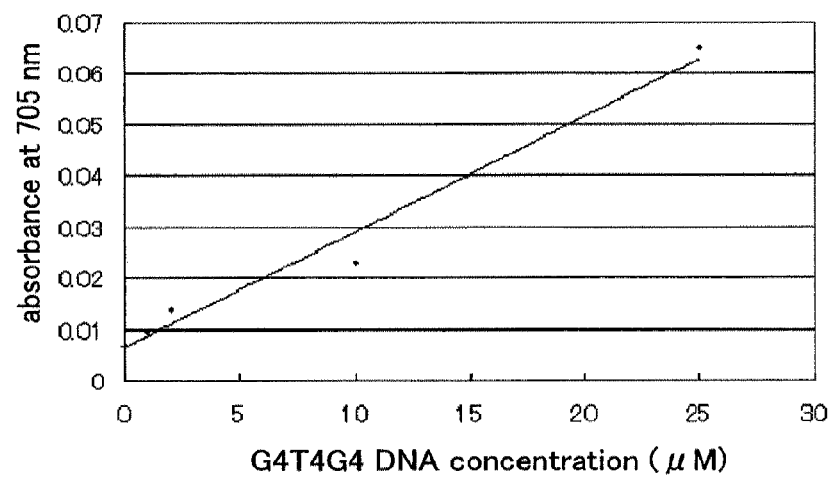
(C)
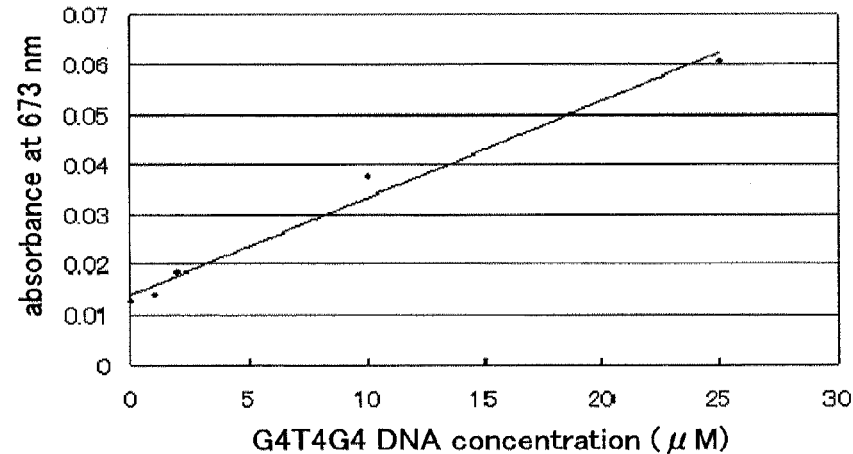

[Fig. 28]
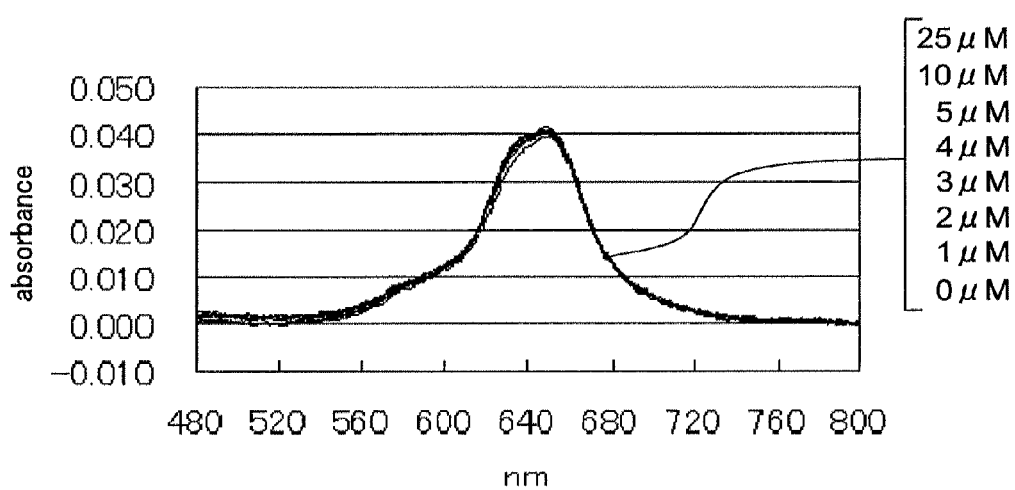

[Fig. 29]

| | structure of each phthalocyanine | G-quadruplex consisting of human telomeric DNA | | G-quadruplex consisting of G4T4G4 DNA | single stranded DNA | double stranded DNA |
|---|---|---|---|---|---|---|
| | | antiparallel type | mixture of parallel type and antiparallel type | parallel type | | |
| anionic copper phthalocyanine | | ○ | ○ | ○ | × | × |
| anionic nickel phthalocyanine | | ○ | ○ | ○ | × | × |
| anionic phthalocyanine without having coordination metal | | ○ | ○ | ○ | × | × |
| anionic iron phthalocyanine | | × | × | × | – | – |
| anionic zinc phthalocyanine | | ○ | ○ | ○ | × | × |
| anionic cobalt phthalocyanine | | ○ | ○ | ○ | × | × |

[Fig. 30]
(A)
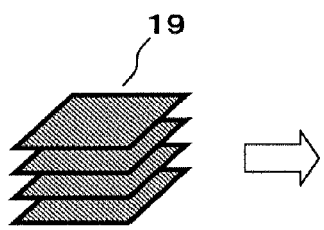
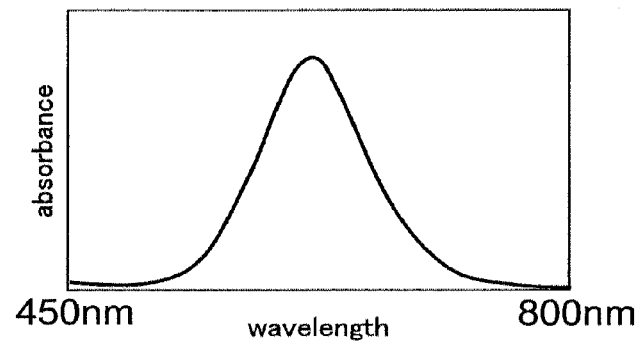
(B)
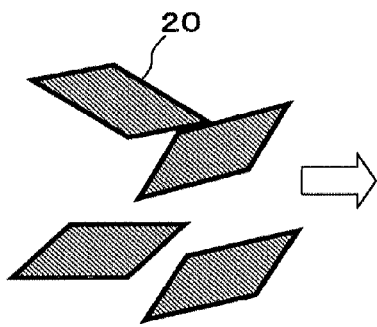
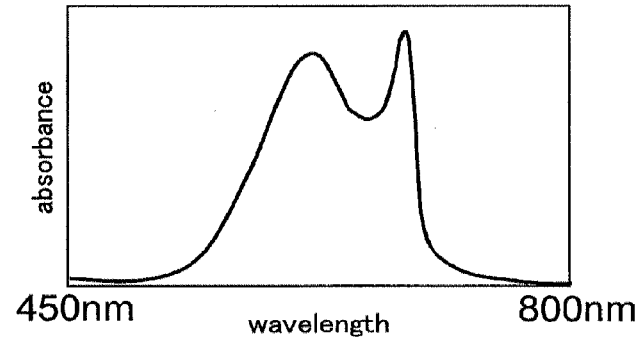

[Fig. 31]
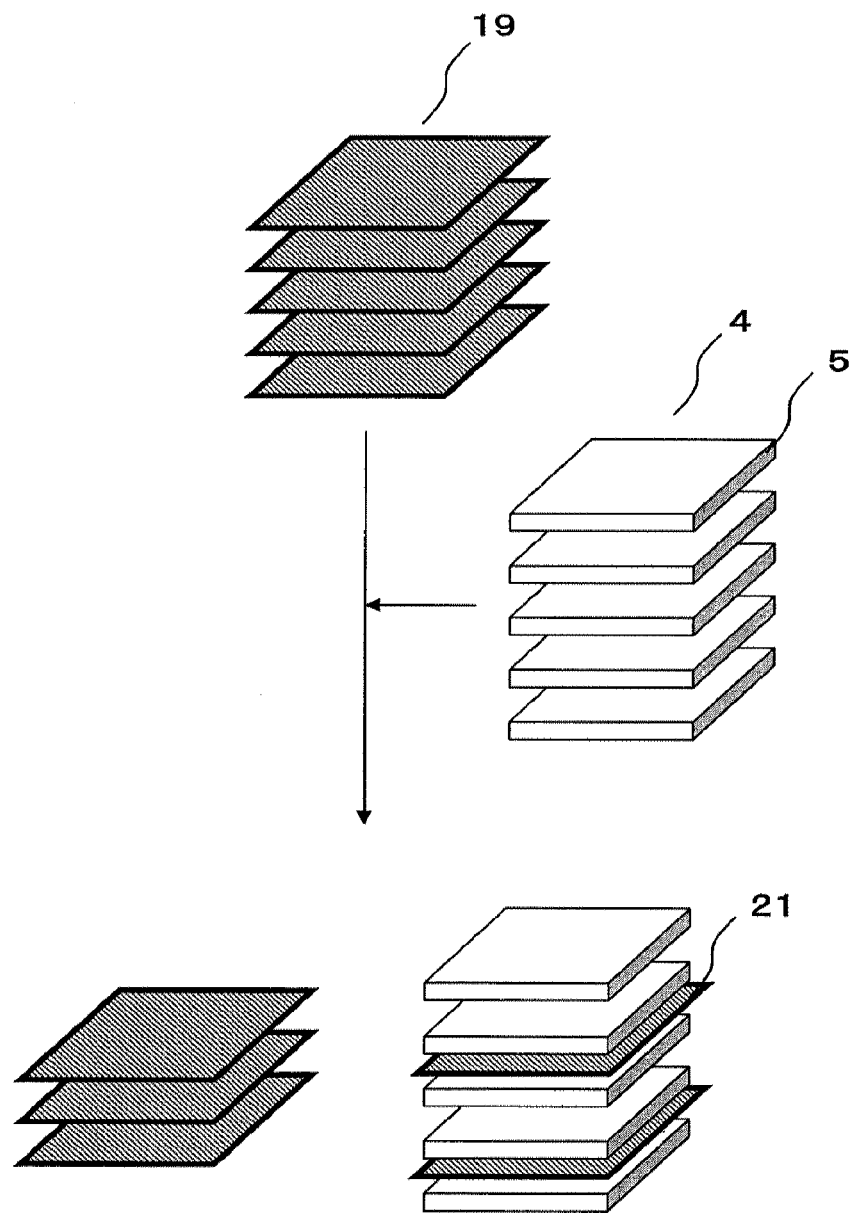

[Fig. 32]
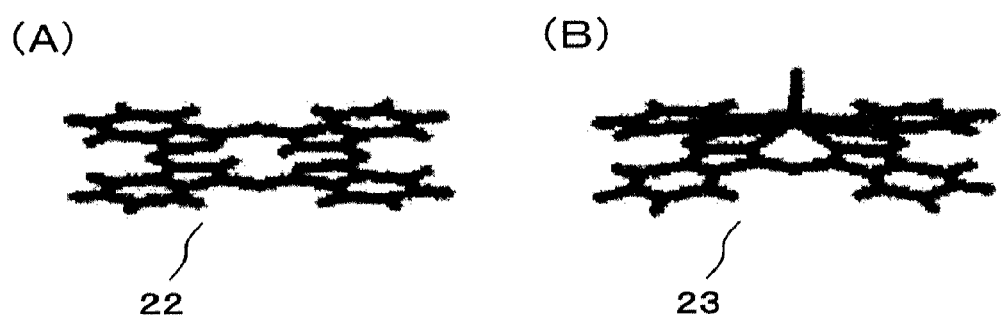

[Fig. 33]
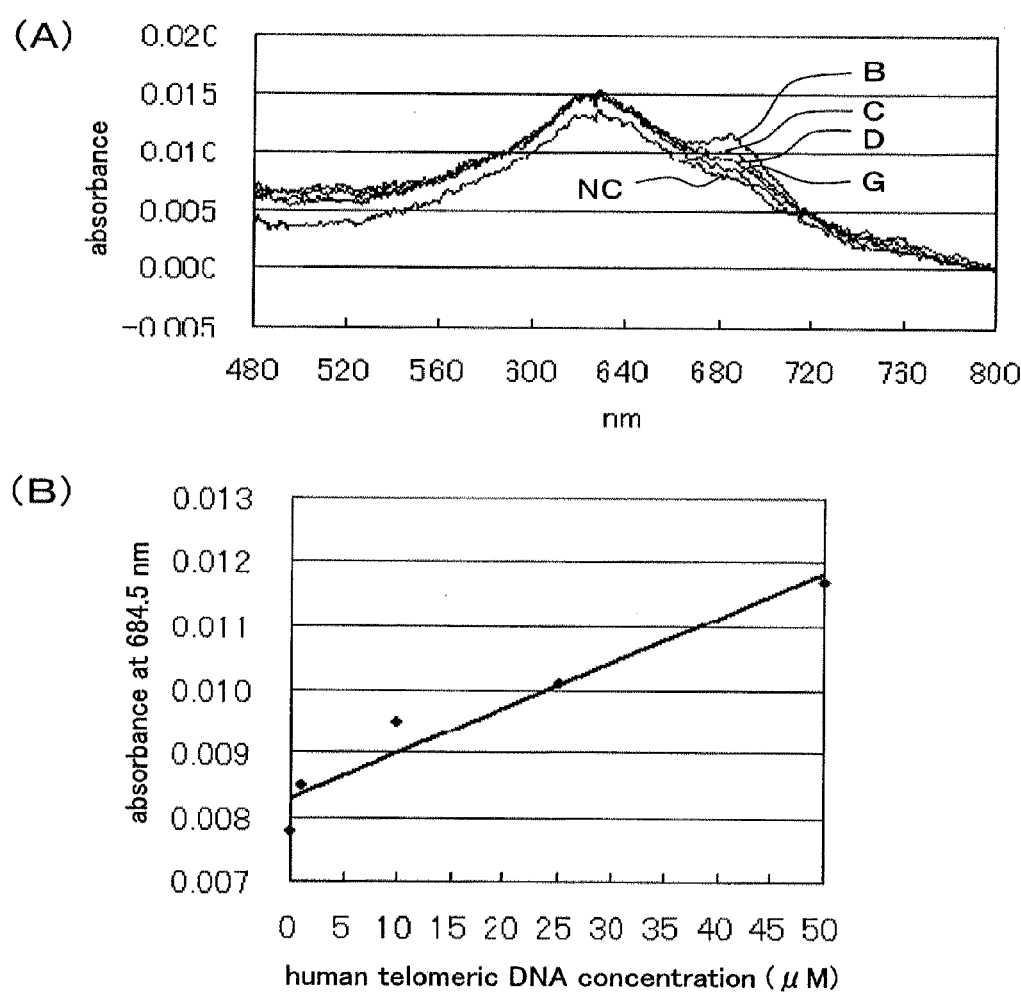

[Fig. 34]
(A)
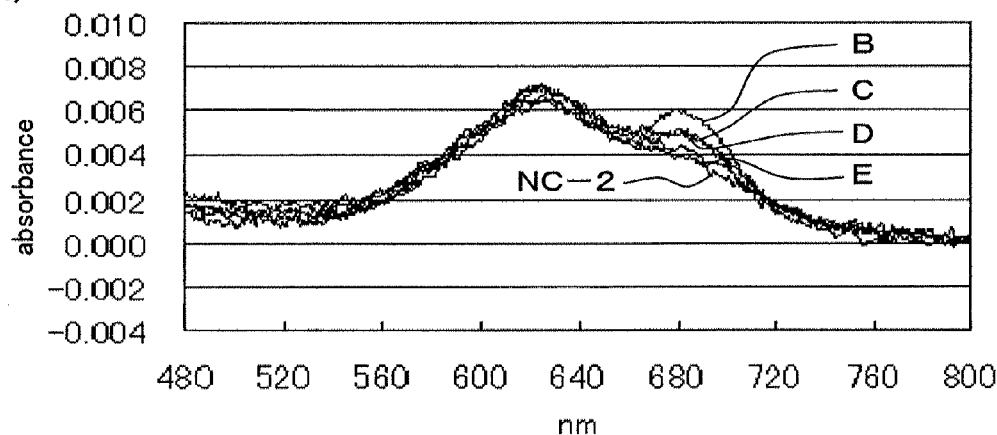
(B)
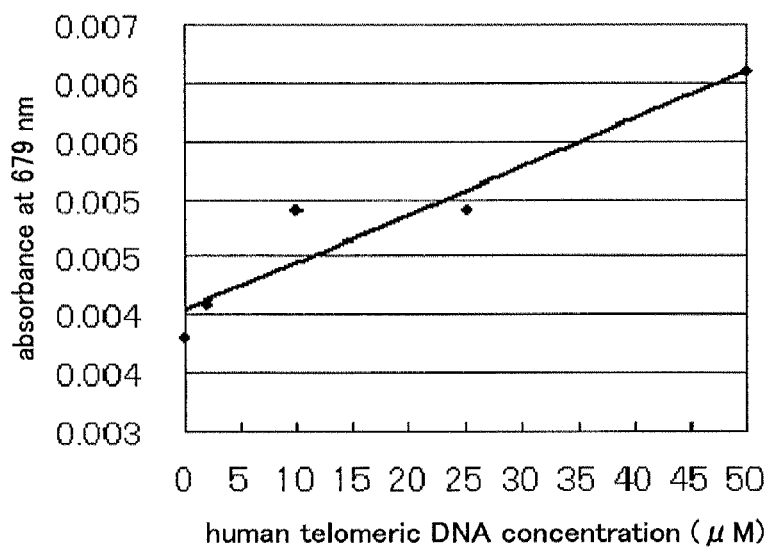

[Fig. 35]
(A)
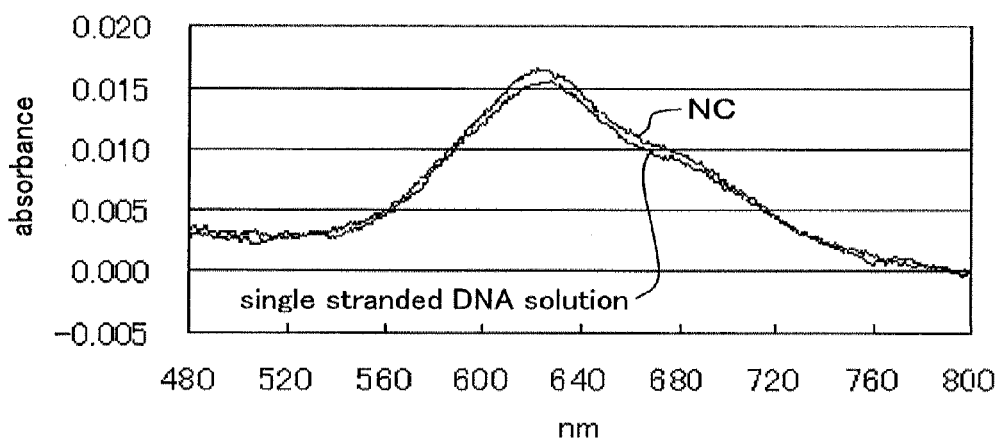
(B)
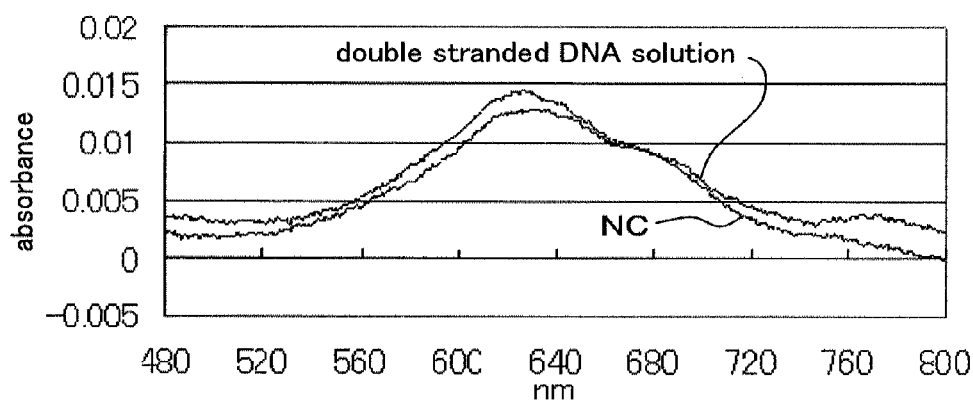

[Fig. 36]
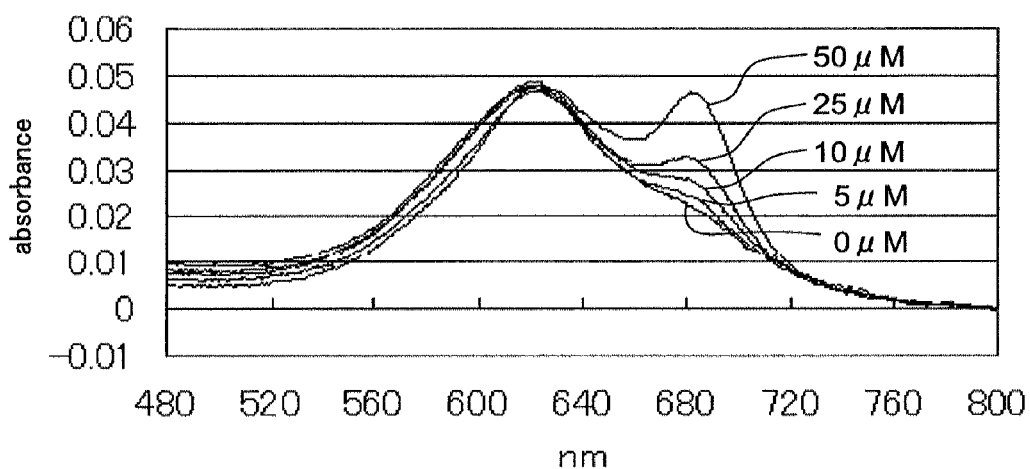
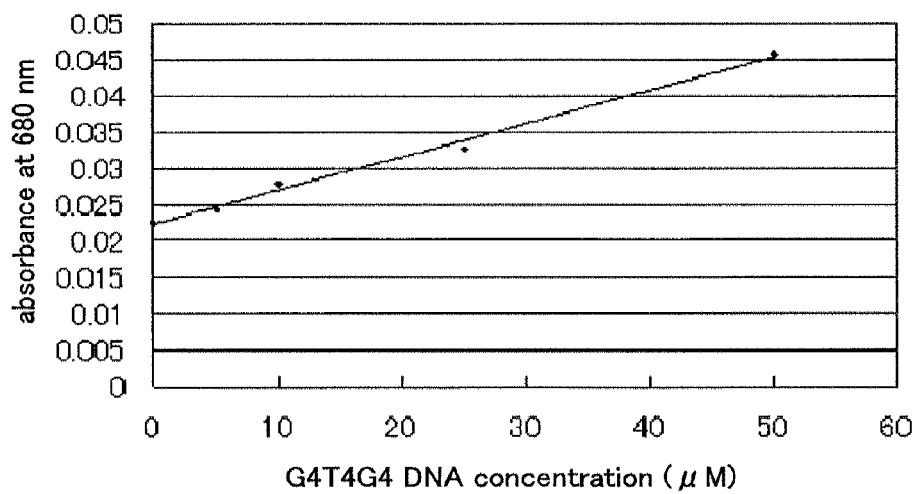

METHOD FOR DETECTING G-QUADRUPLEX, METHOD FOR DETECTING G-QUADRUPLEX-FORMING DNA AND METHOD FOR DETERMINING TELOMERASE ACTIVITY

RELATED APPLICATIONS

This application is a Continuation of U.S. application Ser. No. 12/649,948, filed on Dec. 30, 2009, now U.S. Pat. No. 8,119,347, which is a continuation application under U.S.C. 111(a) of pending prior International application No. PCT/JP2009/002304, filed on May 26, 2009, which in turn claims the benefit of Japanese Application No. 2008-137574 filed on May 27, 2008, the disclosures of which Applications are incorporated by reference herein.

TECHNICAL FIELD

The present invention relates to a detection method of a DNA conformation, and a diagnostic method using the same.

The Sequence listing in "SEQUENCE LISTING.TXT" created on Mar. 17, 2010, being 1.23 KB in size is incorporated by reference.

BACKGROUND ART

Telomere has a structure composed of several proteins and DNAs located at both ends of chromosomes of eucaryotic organisms. Studies carried out hitherto have revealed that the telomere structure protects the chromosomes from a kind of DNA degradative enzyme, inadequate DNA repair, and the like. Furthermore, since the telomeric DNA is shortened with every cell division, it has been believed to play an important role in events referred to as cell aging and immortalization.

On the other hand, telomere is proven to have several features in view of structural aspects. More specifically, in almost all parts of chromosomal DNAs, adenine (hereinafter, referred to as A) base with thymine (hereinafter, referred to as T) base, and guanine (hereinafter, referred to as G) base with cytosine (hereinafter, referred to as C) base specifically form Watson-Crick type base pairs via a hydrogen bond, respectively. A double helix structure is constructed between double DNA strands that are complementary to one another, through causing a $\pi$-$\pi$ stacking interaction among their base pairs (FIG. 1).

However, in telomeric DNA, almost all parts are composed of double strand DNAs that are complementary to one another, whereas the 3' end is overhung and forming a single strand DNA. Although the length of the overhang part and the full length of telomere may vary depending on the species, the overhang has a length of approximately 50-100 bases, while the full length has about 10,000 base pairs at the initial stage in the case of humans. Moreover, other structural feature of the telomere sequence is that the strand having the overhang includes repeating sequences that are rich in G, and thus another stand which is complementary thereto includes repeating sequences that are rich in C.

Specifically, in the case of humans, the strand including the overhang has repeating 5'-TTAGGG-3' (SEQ ID NO: 1), i.e., a G-rich sequence, and another has repeating 5'-CCCTAA-3' (antisense strand of SEQ ID NO: 1), i.e., a C-rich sequence.

In recent years, the G-rich sequence in the telomere site has been particularly extensively studied on the ground that it has been revealed that this sequence can form a quadruple DNA structure referred to as "G-quadruplex". As the G-quadruplex (guanine quadruplex structure), multiple patterns have been known such as: one referred to as a parallel type in which all four DNA strands are oriented to the same direction of from 5' to 3'; or one referred to as an antiparallel type in which two strands are oriented to the same direction while the other two are oriented to the opposite direction, any of which having the features as shown in FIG. 2. In other words, four G bases form a structure referred to as "G quartet" via a Hoogsteen hydrogen bond, and the structure is maintained by a $\pi$-$\pi$ stacking interaction of the G quartet faces.

Moreover, formation of the G-quadruplex structure requires coordination of the metal ions between a G-quartet face and a G-quartet face, and coordination of a K ion, Na ion and the like has been known. Details of formation of such a G-quadruplex in a telomere have been unclear for the present on suitable conditions as well as on the function performed thereby. However, it has been considered that the G-quadruplex would be an important structure that may relate to protection of the chromosome, aging of the cell, and the like.

Still further, it has also been elucidated that the G-rich sequence as described above is present not only in telomeres. For example, also in c-myc which is a carcinogenic gene, are present G-rich sequences that form G-quadruplexes. In addition, other genes such as c-kit, bcl-2, VEGF, H-ras and N-ras gene are found to have G-rich sequences that form a G-quadruplex in the promoter region. These are all genes that relate to malignant transformation and the like of cells, suggesting that the G-quadruplex may play an important role in human bodies. For the present, it is expected that there further exist G-rich sequences being capable of forming G-quadruplexes in the number of over three hundred thousand (hereinafter, such sequence may be referred to as a putative G-quadruplex sequence). There has been increasing interest in whether or not the G-quadruplex is formed therefrom, and the function performed by the structure when it is formed.

One of the most necessary techniques in such technical background is a method for specifically detecting a G-quadruplex. That is, there exists a need for a technique that enables the presence or absence of a G-quadruplex in a DNA in a sample, or the presence or absence of possibility of practical formation of a G-quadruplex from a DNA constituted with the putative G-quadruplex sequence in the sample to be determined. For example, in an attempt to determine the former by way of a prior art, the following may be illustrated. That is, a sample solution including a target DNA is provided, and a CD (Circular Dichroism) spectrum of this solution is measured. Then, an analysis may be made as to whether or not thus obtained CD spectrum is peculiar to the G-quadruplex. However, apparatuses for measuring the CD spectrum are very expensive and of large size. In addition, a long period of time of approximately 30 min is required for the analysis, and the number of the samples which can be analyzed in one trial is usually one; therefore, this technique is significantly inferior in terms of high throughput performance. Further, depending on the shape of the quadruplex, there may be a problem of failure in distinguishing the DNA from those having other forms by using CD.

As a means for resolving such a problem, a method may be referred to in which a probe material that generates a signal (absorbance, fluorescence intensity, etc.), which can be analyzed with an inexpensive apparatus depending on the presence or absence of a G-quadruplex, is mixed in the solution beforehand, and the signal in this solution is detected, as shown in FIG. 3. In such a method, specificity for the G-quadruplex of this probe would be of importance. More specifically, since a genomic DNA includes therein both a double stranded DNA structure that accounts for a large proportion of the same, and a single stranded DNA structure typified by the aforementioned overhang of a telomere, specificity for the G-quadruplex over these structures is important in comparison to these structures. The reason for this importance is that irrespective of the contemplation for determining the presence or absence of only the G-quadruplex, accurate detection of a G-quadruplex in a solution would be difficult when a signal is generated upon interaction of the probe also with any of the single stranded and double stranded DNAs, as a result of low specificity for the G-quadruplex of the probe.

In addition, when a prior art is used for examining a DNA of the putative G-quadruplex sequence in a sample with respect to formation of a G-quadruplex in effect, the process as shown in FIG. 4 would be employed. More specifically, a DNA having the putative G-quadruplex sequence is provided in a solution. Thereafter, this solution is maintained under a condition for permitting a G-quadruplex forming reaction, thereby allowing a G-quadruplex-forming reaction to be carried out. Then, the analysis on the presence or absence of a G-quadruplex in the solution following the reaction may be performed by measuring a CD spectrum. However, there can be accompanied by problems of the apparatus being expensive and of large scale, and in terms of high throughput, as described above also in this process. Thus, a probe for G-quadruplex detection as shown in FIG. 3 would be very useful if available, also in this case.

Specifically, this probe is mixed with the solution after the G-quadruplex-forming reaction described above, and the signal generated as a result may be measured, as shown in FIG. 5. In this process, since the DNA of the putative G-quadruplex sequence before the G-quadruplex-forming reaction can be any of single stranded and double stranded DNAs as described above, specificity of the probe for the G-quadruplex is extremely important. That is, accurate detection of the formed G-quadruplex becomes difficult when the aforementioned probe interacts also with the original structure (single strand or double stranded DNA) of the DNA of the putative G-quadruplex sequence to generate a signal, in the case in which the DNA of the putative G-quadruplex sequence did not form a G-quadruplex at all after the G-quadruplex-forming reaction, or in the case in which such formation was only partially executed. To the contrary, when the specificity of the probe for a G-quadruplex is extremely high, mixing of the probe in the solution prior to the G-quadruplex-forming reaction is permitted, and complication of the operation can be also obviated in the method shown in FIG. 5.

As described in the foregoing, the G-rich sequence that forms a G-quadruplex has been found in sites relating to cancer, aging or the like in chromosomes. Therefore, it is expected that disease diagnoses can be realized in future by identifying a G-quadruplex in a chromosome of a patient. Accordingly, development of a method for specifically detecting a G-quadruplex can be deemed as a very important problem. In addition, as characteristic features of the probe, it would be more advantageous of course, when the probe not only can detect a G-quadruplex or a DNA of the putative G-quadruplex sequence specifically but can yield a change such as increase or decrease of the signal depending on the amount of them being present, since not only mere a detection but also quantitative analysis is enabled.

Additionally, an enzyme referred to as telomerase has been known. This enzyme is a complex composed of an RNA and reverse transcriptase etc., whereby the repeating sequence in the G-rich strand at the telomere site which is shortened upon cell division can be replicated and thus extension is permitted (i.e., in the case of human, telomerase adds a 5'-TTAGGG-3' sequence (SEQ ID NO: 1); hereinafter, this addition reaction being referred to as telomerase reaction). This enzyme is not usually found in human common somatic cells, but it is known to be expressed in a large amount in germ cells as well as most cancer cells. Thus, the occurrence or absence of malignant transformation of a subject cell can be examined using the telomerase activity as a marker.

As a conventional method for this purpose, a process referred to as TRAP assay has been known. The TRAP assay is explained below with reference to FIG. 6. In the TRAP assay, a solution containing a synthetic single stranded DNA provided as a template for telomerase is prepared first. This single stranded DNA usually consists of a sequence of 5'-AATCCGTCGAGCAGAGTT-3' (SEQ ID NO: 2), which is referred to as TS primer. Accordingly, telomerase achieves addition of the 5'-TTAGGG-3' sequence (SEQ ID NO: 1) to the 3' end of this TS primer (see, NPL 3). It should be noted that this TS primer is not limited to this sequence, but any single stranded DNA that serves as a template of telomerase is acceptable.

Next, into this solution is added an extract from a cell sample or a tissue sample to which malignant transformation is suspected. After mixing, the solution is maintained under a condition in which a telomerase reaction can be permitted. In this step, provided that the sample is subject to malignant transformation, the telomerase reaction is caused from the TS primer as an origin since there exists a telomerase activity. To the contrary, the telomerase reaction is not caused without malignant transformation. Then, the DNA elongated by the telomerase reaction is finally amplified by PCR, and thus amplified DNA fragment is detected by an electrophoretic technique.

Since the lengths of DNAs obtained by the telomerase reaction vary widely, the obtained electrophoretic image may be as shown in FIG. 7. More specifically, when the used sample has a potent telomerase activity, the obtained DNA fragments appear as ladder bands representing the lengths within a broad range from short to long, with the color density of the bands more likely to be higher. To the contrary, since a long DNA fragment cannot be obtained from telomerase having a weak activity, ladder bands appear representing the lengths in a short range, with the color density of the bands more likely to be lower. Therefore, for identifying the malignant transformation of the sample, the range of the lengths, and the color density of the band of the DNA fragments on the electrophoretic image obtained as a result of the TRAP assay may be analyzed. However, quantitative analyses of these have been still difficult; therefore, merely a qualitative evaluation is attainable.

In these respects, when the probe for specific detection of a G-quadruplex illustrated in FIG. 3 and FIG. 5 is not only merely specific for the G-quadruplex, but can alter its signal intensity depending on the amount of the G-quadruplex being present, such a probe can be useful also in diagnoses of cancer using the telomerase activity as a marker. The flowchart of such a diagnosis is shown in FIG. 8.

Also in this method, the following steps are carried out in a similar manner to those in the operation shown in FIG. 6: preparing a solution containing a TS primer first; adding an extract from a cell sample or a tissue sample into this solution next, followed by mixing; then subjecting this solution to a telomerase reaction, and thereafter amplifying with a PCR method the DNA elongated by the telomerase reaction. However, in the method shown in FIG. 8, the solution after the PCR is not subjected to electrophoresis, but is subjected to a G-quadruplex-forming reaction similarly to the case shown in FIG. 5. Consequently, thus formed G-quadruplex is detected using a probe for G-quadruplex detection. The amount of the formed G-quadruplex reflects the intensity of the telomerase activity in this step; therefore, this method enables quantitative analysis of the telomerase activity and identification of malignant transformation, provided that the probe can alter its signal intensity depending on the amount of the G-quadruplex.

Needless to say, specificity of the probe for a G-quadruplex is also extremely important in such a method. That is, when the cell sample is not subject to malignant transformation, the telomerase reaction does not proceed. As a result, the TS primer being a single stranded DNA remains unchanged in the reaction liquid. Furthermore, the following PCR reaction does not also proceed, and thus the primer for the PCR reaction remains in the state of the single stranded DNA. Therefore, when the cell sample is not subject to malignant transformation, a large amount of single stranded DNAs will be finally present in the reaction mixture, whereby quantitative analyses of the telomerase activity and diagnoses of cancer may be difficult due to a signal generated from the probe via a reaction with these single stranded DNAs.

specifically interacts with a G-quadruplex, and can alter the signal depending on the amount of the G-quadruplex.

For example, PTL 1 proposes a novel compound that is specific for a G-quadruplex. Certainly, this probe is highly selective for binding to a G-quadruplex as compared with single stranded and double stranded DNAs; but binding to the single stranded and double stranded DNAs can be also identified.

In addition, NPL 1 describes specificity for a G-quadruplex of a cationic porphyrin having a structure represented by the following chemical formula 1. In NPL 1, a phenomenon of SPR (surface plasmon resonance) is utilized to analyze binding on a gold substrate the porphyrin with a DNA having a double stranded structure, or with a G-quadruplex. As a result, it is sure that the alteration of the signal is greater with the G-quadruplex compared to with the double stranded DNA, but the alteration of the signal is also observed with the double stranded DNA, thereby leading to failure in observation with sufficient specificity.

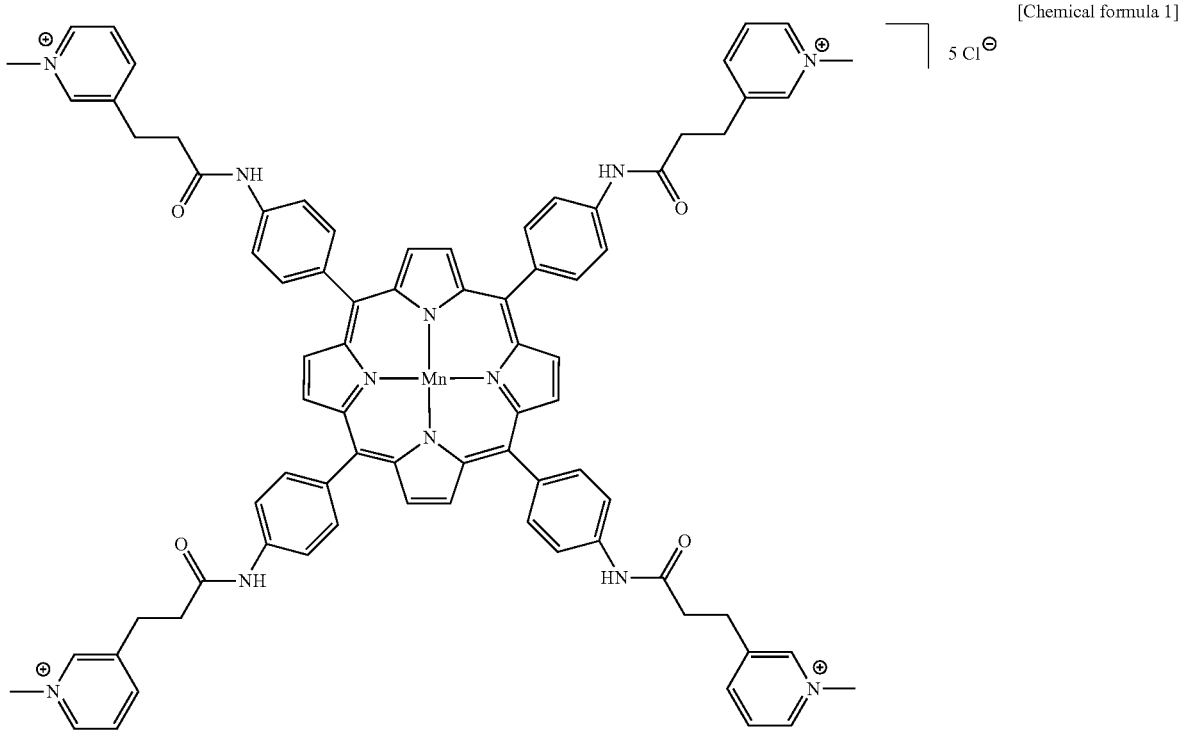

[Chemical formula 1]

As explained in the foregoing, a method that enables specific detection of a G-quadruplex is very useful even in a state in which any one of single stranded and double stranded DNAs can be present in the solution. Moreover, when a quantitative performance is available, problems in conventional TRAP assays can be solved, in addition to enabling quantitative detection of a G-quadruplex. Under such circumstances, development of a method for detecting a G-quadruplex has been actively attempted using a probe that Furthermore, NPL 2 reports specificity of a cationic porphyrin having a structure represented by the following Chemical formula 2 or Chemical formula 3 for a G-quadruplex. Also in this NPL 2, analyses of a SPR phenomenon or a ultraviolet visible absorption spectrum are carried out to determine specific binding of these porphyrins to a G-quadruplex. However, it is described that double stranded DNAs and these porphyrins may nonspecifically bound under conditions of the DNA concentration being no lower than 5 µM.

[Chemical formula 2]

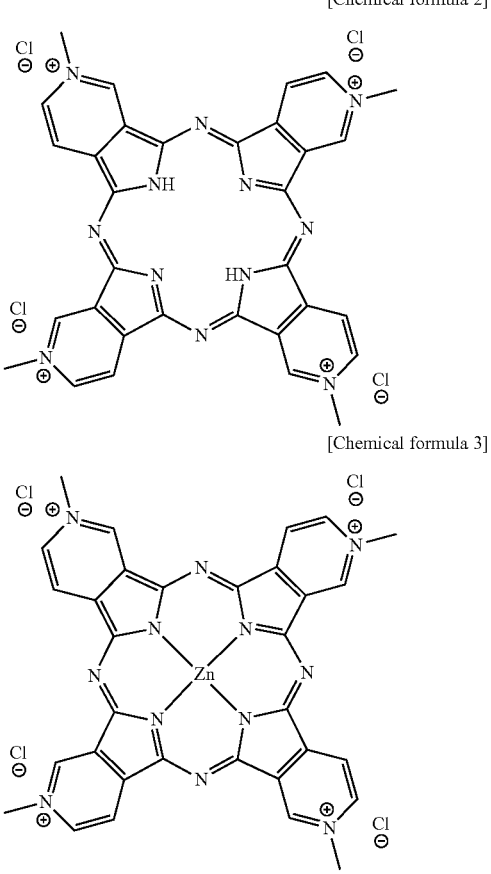

[Chemical formula 3]

As described above, the probes developed heretofore in attempts to detect a G-quadruplex are all cationic. This would be based on the idea that cationic probes can be very advantageous taking into consideration of the G-quadruplex which is anionic. That is, an anionic probe will cause electrostatic repulsion, which can be disadvantageous in binding reactions. Since not only a G-quadruplex but all DNA strands are anionic, for the development of probes targeting to the same, the most important design guide will be directed to provide cationic one, leading to preclusion of an idea to provide anionic one.

CITATION LIST

Patent Literature

[PTL 1]
Pamphlet of PCT International Publication No. 2004/072027

Non Patent Literature

[NPL 1]
J. Am. Chem. Soc., 129, 1502-1503
[NPL 2]
Chem. Commun. 4685-4687
[NPL 3]
Nucleic Acids Res., 25, 2595-2597

SUMMARY OF INVENTION

Technical Problem

As described in the foregoing, a method which enables a G-quadruplex to be specifically detected in a state in which any of single stranded and double stranded DNAs can be present in a solution is very useful. In addition, when the method is further accompanied by a quantitative performance, quantitative detection of a G-quadruplex can be achieved, and also, problems of conventional TRAP assays can be solved. For this purpose, development of a method for detecting a G-quadruplex has been actively attempted using a probe that specifically interacts with a G-quadruplex, and can alter the signal depending on the amount of the G-quadruplex, but any of the methods proposed hitherto cannot provide specific detection of a G-quadruplex. Under such circumstances, the present inventors elaborately investigated, and consequently found that an anionic planar phthalocyanine interacts with a G-quadruplex in an extremely highly specific manner, despite being its anionicity, and yields varying absorbance depending on the concentration of the G-quadruplex. Accordingly, the present invention has been accomplished.

Solution to Problem

In an aspect of the present invention which can solve the foregoing problems, there is provided a method for detecting a G-quadruplex in a sample solution including a DNA forming at least any one or more structures of a single stranded structure, a double stranded structure and a G-quadruplex structure, the method including the steps of:

(a) preparing a solution comprising an anionic planar phthalocyanine;

(b) mixing the solution comprising an anionic planar phthalocyanine with the sample solution;

(c) measuring the absorbance at 640 to 740 nm of a liquid mixture obtained following the step (b); and (d) determining that a DNA forming a G-quadruplex structure is included in the sample solution when a peak having an absorption maximum at 640 to 740 nm appears, in this order.

Further, in another aspect of the present invention, there is provided a method for detecting a G-quadruplex-forming DNA by determining the ability of a DNA forming any one or more structures of a single stranded structure and a double stranded structure included in a sample solution to form a G-quadruplex, the method including the steps of:

(a) maintaining the sample solution under a condition for permitting a G-quadruplex forming reaction;

(b) preparing a solution comprising an anionic planar phthalocyanine;

(c) mixing the solution comprising an anionic planar phthalocyanine with the sample solution either before or after the step (a);

(d) measuring the absorbance at 640 to 740 nm of the liquid mixture following a series of the steps of (a) to (c); and (e) determining that a DNA forming a G-quadruplex structure is included in the sample solution when a peak having an absorption maximum at 640 to 740 nm appears, in this order.

Moreover, in further aspect of the present invention, there is provided a method for determining a telomerase activity in a sample solution, the method including the steps of:
(a) preparing the sample solution;
(b) preparing a substrate solution comprising a DNA that serves as a substrate for telomerase;
(c) mixing the sample solution with the substrate solution to prepare a telomerase reaction solution;
(d) maintaining the telomerase reaction solution under a condition to allow a DNA addition reaction to be performed by telomerase;
(e) preparing a solution comprising an anionic planar phthalocyanine;
(f) mixing the solution comprising an anionic planar phthalocyanine with a solution obtained following the step (d);
(g) measuring the absorbance at 640 to 740 nm of the liquid mixture obtained following a series of the steps of (a) to (f); and
(h) determining that a DNA forming a G-quadruplex structure is included in the sample solution when a peak having an absorption maximum at 640 to 740 nm appears,
in this order.

In the present invention, the anionic planar phthalocyanine may be an anionic planar phthalocyanine having copper, zinc, cobalt or nickel as a coordination metal, or an anionic planar phthalocyanine not having a coordination metal.

Additionally, in the present invention, the anionic planar phthalocyanine preferably has at least one functional group obtained from the group consisting of a carboxyl group, a metal salt of a carboxyl group, a sulfo group, and a metal salt of a sulfo group.

The objects described in the foregoing, other objects, features and advantages of the present invention will be apparent from the following detailed description of preferred embodiments with reference to attached drawings.

Advantageous Effects of Invention

According to the present invention, a method for specifically and quantitatively detecting a G-quadruplex, a method for detecting a DNA specifically and quantitatively which can form a G-quadruplex, and a method for determining a telomerase activity are provided.

BRIEF DESCRIPTION OF DRAWINGS

FIG. 1 shows a diagram for illustrating the structure of a double stranded DNA;
FIG. 2 shows a diagram for illustrating the structure of a G-quadruplex;
FIG. 3 shows a diagram for illustrating a method for specifically detecting a G-quadruplex-forming DNA using a G-quadruplex-forming DNA specific probe;
FIG. 4 shows a diagram for illustrating a method for detecting a putative G-quadruplex sequence using an apparatus for a CD analysis;
FIG. 5 shows a diagram for illustrating a method for detecting a putative G-quadruplex sequence using a G-quadruplex-forming DNA specific probe;
FIG. 6 shows a diagram for illustrating a conventional method for determining a telomerase activity;
FIG. 7 shows a diagram for illustrating one example of an electrophoretic image obtained by a conventional method for determining a telomerase activity;
FIG. 8 shows a diagram for illustrating a method for determining a telomerase activity using a G-quadruplex-forming DNA specific probe;
FIG. 9 shows a diagram for illustrating a method for the specific detection of a G-quadruplex-forming DNA using an anionic phthalocyanine;
FIGS. 10A and 10B show diagrams for illustrating a method for detecting a putative G-quadruplex sequence using anionic phthalocyanine;
FIG. 11 shows a diagram for illustrating a method for determining a telomerase activity using an anionic phthalocyanine;
FIG. 12 shows a diagram for illustrating results of the CD measurement in Example 2;
FIGS. 13A and 13B show diagrams for illustrating results in the case of using an anionic copper phthalocyanine in Example 2;
FIGS. 14A and 14B show diagrams for illustrating results in the case of using an anionic nickel phthalocyanine in Example 2;
FIGS. 15A, 15B and 15C show diagrams for illustrating results in the case of using an anionic phthalocyanine not having a coordination metal in Example 2;
FIG. 16 shows a diagram for illustrating results in the case of using an anionic iron phthalocyanine in Example 2;
FIG. 17 shows a diagram for illustrating results of the CD measurement in Example 1;
FIGS. 18A and 18B show diagrams for illustrating results in the case of using an anionic copper phthalocyanine in Example 1;
FIGS. 19A and 19B show diagrams for illustrating results in the case of using an anionic nickel phthalocyanine in Example 1;
FIGS. 20A, 20B and 20C show diagrams for illustrating results in the case of using an anionic phthalocyanine not having a coordination metal in Example 1;
FIG. 21 shows a diagram for illustrating results in the case of using an anionic iron phthalocyanine in Example 1;
FIGS. 22A and 22B show diagrams for illustrating results in the case of using an anionic copper phthalocyanine in Example 3;
FIGS. 23A and 23B show diagrams for illustrating results in the case of using an anionic nickel phthalocyanine in Example 3;
FIGS. 24A and 24B show diagrams for illustrating results in the case of using an anionic phthalocyanine not having a coordination metal in Example 3;
FIGS. 25A and 25B show diagrams for illustrating results in the case of using an anionic copper phthalocyanine in Example 4;
FIGS. 26A and 26B show diagrams for illustrating results in the case of using an anionic nickel phthalocyanine in Example 4;
FIGS. 27A, 27B and 27C show diagrams for illustrating results in the case of using an anionic phthalocyanine not having a coordination metal in Example 4;
FIG. 28 shows a diagram for illustrating results in the case of using an anionic iron phthalocyanine in Example 4;
FIG. 29 shows a drawing that summarizes results of the present Examples 1 to 4;
FIGS. 30A and 30B show drawings for illustrating a typical absorbance spectrum in the case in which phthalocyanine is associated or dispersed;
FIG. 31 shows a diagram for illustrating a mechanism according to the present invention;
FIGS. 32A and 32B show views for illustrating a planar phthalocyanine and a shuttlecock type phthalocyanine;

FIG. 33 shows a diagram for illustrating results in the case of using an anionic cobalt phthalocyanine in Example 1;

FIGS. 34A and 34B show diagrams for illustrating results in the case of using an anionic cobalt phthalocyanine in Example 2;

FIGS. 35A and 35B show diagrams for illustrating results in the case of using an anionic cobalt phthalocyanine in Example 3; and FIGS. 36A and 36B show diagrams for illustrating results in the case of using an anionic cobalt phthalocyanine in Example 4.

DESCRIPTION OF EMBODIMENTS

Hereinafter, embodiments of the present invention will be explained with reference to FIGS. 9 to 11.

Embodiment 1

In the present Embodiment 1, a method for detecting a G-quadruplex in a sample solution including a DNA forming at least any one or more structures of a single stranded structure, a double stranded structure and a G-quadruplex structure is explained with reference to FIG. 9.

In this Embodiment 1, the sample solution is first mixed with a solution including an anionic planar phthalocyanine. Then, the absorbance of this mixed solution at a specified wavelength in the range of 640 to 740 nm is subsequently measured. In this step, when a DNA forming a G-quadruplex is present in the sample solution, an absorption peak depending thereon appears in the range of 640 to 740 nm. However, in contrast, even though a DNA having a single stranded structure or a double stranded structure is present, any peak depending thereon does not appear in the range of the aforementioned wavelength. Therefore, by analyzing the presence or absence of this peak, it can be seen that a DNA forming a G-quadruplex was present in the sample solution or not.

In order to analyze the presence or absence of the peak, for example, a reference solution which has been known that at least a DNA forming a G-quadruplex is not included is prepared, which reference solution is also subjected to the measurement of the absorbance in the specified wavelength as described above after mixing with the solution including an anionic planar phthalocyanine. Then, the difference between thus derived absorbance value and the absorbance value derived when the sample solution was used may be determined.

In addition, the absorbance value at the absorption peak increases as the concentration of the DNA forming a G-quadruplex becomes higher. Therefore, by analyzing the absorbance, analysis of the concentration of the DNA forming a G-quadruplex is enabled.

The anionic planar phthalocyanine used in Embodiment 1 may be an anionic planar phthalocyanine having copper, zinc, cobalt or nickel as a coordination metal, or an anionic planar phthalocyanine not having a coordination metal.

Additionally, the anionic planar phthalocyanine used in Embodiment 1 has at least one functional group obtained from the group consisting of a carboxyl group, a metal salt of a carboxyl group, a sulfo group, and a metal salt of a sulfo group.

Furthermore, the specified wavelength as described above may be any wavelength as long as it falls within the range of 640 to 740 nm, but a wavelength more approximate to the maximal value of the appearing peak is more preferred since measurement with higher sensitivity is permitted.

Embodiment 2

In the present Embodiment 2, the method for determining the ability of a DNA forming any one or more structures of a single stranded structure and a double stranded structure included in a sample solution to form a G-quadruplex is explained with reference to FIG. 10.

In the present Embodiment 2, the sample solution is first mixed with a solution including an anionic planar phthalocyanine, and the mixture is maintained under a condition for permitting G-quadruplex formation to allow a G-quadruplex-forming reaction to be performed. Thereafter, the absorbance of this mixed solution at a specified wavelength in the range of 640 to 740 nm is measured (FIG. 10 (A)), or alternatively, after allowing a G-quadruplex-forming reaction to be performed by maintaining the sample solution under a condition for permitting G-quadruplex formation, and then mixing with the solution including an anionic planar phthalocyanine, the absorbance of this mixed solution at a specified wavelength in the range of 640 to 740 nm is measured (FIG. 10 (B)). In this step, when a DNA forming a G-quadruplex is present in the mixed solution similarly to the Embodiment 1 described above, an absorption peak depending thereon appears in the range of 640 to 740 nm. Moreover, the absorbance value at the absorption peak increases as the concentration of the DNA forming a G-quadruplex becomes higher.

However, in contrast, even though a DNA having a single stranded structure or a double stranded structure is present in this mixed solution, any peak depending thereon does not appear in this range of the wavelength. Therefore, by analyzing the presence or absence of this peak, it can be seen whether the DNA in the sample solution formed a G-quadruplex or not. As a means for analyzing the presence or absence of the peak, for example: a reference solution not including a DNA, or including only a DNA not forming a G-quadruplex even though a DNA is included is prepared; the absorbance value is measured for this reference solution via the step completely the same as the case of the aforementioned sample solution, and the difference from the absorbance value obtained in the case of the sample solution may be determined.

In addition, the absorbance value at the absorption peak increases as the concentration of the DNA forming a G-quadruplex becomes higher. Therefore, by analyzing the absorbance, the concentration in the sample of the DNA that formed the G-quadruplex can be quantitatively analyzed.

Similarly to Embodiment 1, the anionic planar phthalocyanine used in the Embodiment 2 may be an anionic planar phthalocyanine having copper, zinc, cobalt or nickel as a coordination metal, or an anionic planar phthalocyanine not having a coordination metal.

Additionally, the anionic planar phthalocyanine used in the Embodiment 2, similarly to Embodiment 1, has at least one functional group obtained from the group consisting of a carboxyl group, a metal salt of a carboxyl group, a sulfo group, and a metal salt of a sulfo group.

Furthermore, the specified wavelength as described above may be any wavelength as long as it falls within the range of 640 to 740 nm, but a wavelength more approximate to the maximal value of the appearing peak is more preferred since measurement with higher sensitivity is permitted.

Embodiment 3

In the present Embodiment 3, a method for quantitatively analyzing a telomerase activity in a sample is explained with reference to FIG. 11.

In the present Embodiment 3, the sample is first mixed with a solution including a single stranded DNA that serves as a substrate for telomerase, and the mixed solution is maintained under a condition to allow a telomerase reaction to be performed. In this step, when activated telomerase is included in the sample, the telomerase reaction is performed by maintaining this condition, and as a result, a DNA consisting of 5'-TTAGGG-3' is added from the aforementioned single stranded DNA as a substrate, while, when any activated telomerase is not present in the sample to the contrary, such DNA addition is not executed.

Then, the mixed solution following the telomerase reaction is subsequently maintained under a condition for permitting G-quadruplex formation. In this step, provided that activated telomerase is included in the sample, and thus the telomerase reaction proceeded, the G-quadruplex is formed, and the amount thereof depends on the telomerase activity in the sample. That is, a greater activity results in a larger amount of the G-quadruplex formed. To the contrary, for example, when the activated telomerase is not included in the sample, as a result, any G-quadruplex is not formed in this step when the telomerase reaction is not carried out.

Then, the mixed solution following the G-quadruplex-forming reaction is finally mixed with a solution including an anionic planar phthalocyanine, the absorbance of this solution at a specified wavelength in the range of 640 to 740 nm may be measured. In this step, when a DNA forming a G-quadruplex is present in the mixed solution similarly to the Embodiments 1 and 2 described above, an absorption peak depending thereon appears in the range of 640 to 740 nm. Moreover, the absorbance value at the absorption peak increases as the concentration of the DNA forming a G-quadruplex becomes higher. However, in contrast, even though a DNA having a single stranded structure or a double stranded structure is present in this mixed solution, any peak depending thereon does not appear in this range of the wavelength. Therefore, by measuring the absorbance value of this peak, the telomerase activity in the sample can be quantitatively analyzed.

In this step, although the aforementioned anionic planar phthalocyanine solution was added to the mixed solution following the G-quadruplex-forming reaction in FIG. 11, timing when the anionic planar phthalocyanine solution is added is not limited thereto. In other words, it may be added at any timing to the mixed solution including the sample solution as long as the timing is following the telomerase reaction, and prior to the measurement of the absorbance.

Similarly to Embodiment 1 and Embodiment 2, the anionic planar phthalocyanine used in the Embodiment 3 may be an anionic planar phthalocyanine having copper, zinc, cobalt or nickel as a coordination metal, or an anionic planar phthalocyanine not having a coordination metal.

Additionally, the anionic planar phthalocyanine used in the Embodiment 3, similarly to Embodiment 1 and Embodiment 2, has at least one functional group obtained from the group consisting of a carboxyl group, a metal salt of a carboxyl group, a sulfo group, and a metal salt of a sulfo group.

Furthermore, the specified wavelength as described above may be any wavelength as long as it falls within the range of 640 to 740 nm, but a wavelength more approximate to the maximal value of the appearing peak is more preferred since measurement with higher sensitivity permitted.

EXAMPLES

The DNAs used in Examples described below are all synthetic products from Hokkaido System Science Co., Ltd. Among the phthalocyanines used in the present Examples, Copper (II) phthalocyanine-3,4',4'',4'''-tetrasulfonic acid tetrasodium salt and Nickel (II) phthalocyanine tetrasulfonic acid tetrasodium salt and Iron (III) phthalocyanine-4,4',4'', 4'''-tetrasulfonic acid, compound with oxygen monosodium salt hydrate were purchased from Sigma-Aldrich Corporation. Phthalocyanine tetrasulfonic acid and Zinc (II) phthalocyanine tetrasulfonic acid were purchased from Funakoshi Co., Ltd. Cobalt (II) phthalocyanine tetracarboxylic acid was synthesized. The synthesis method is as in the following.

Trimellitic acid in an amount of 6.4 g, 20 g of urea, 4.75 g of cobalt chloride hexahydrate and 0.82 g of ammonium molybdate tetrahydrate were heated in 100 ml of nitrobenzene in an oil bath at 170 to 180° C. for 4.5 hrs. After standing to cool, the nitrobenzene layer was removed by decantation. The residual matter was washed with methanol and water, followed by vacuum drying to obtain a solid matter of 8.66 g. After this solid matter in an amount of 1.0 g was stirred in 30 g of a 50% aqueous potassium hydroxide solution at 70 to 75° C. for 2 hrs, 90 ml of water was added and the mixture was stirred, followed by filtration. To thus resulting filtrate was added 35 to 37% hydrochloric acid, thereby making the solution strongly acidic to allow precipitates to be deposited, which were then taken by filtration. The precipitates were dissolved in 100 ml of a 1 N aqueous sodium hydroxide solution, followed by filtration again. Thus resulting filtrate was again made strongly acidic with hydrochloric acid, and the deposited precipitates were taken by filtration. These were washed with a large quantity of water, and thereafter cobalt (II) phthalocyanine tetracarboxylic acid was obtained as a powder of 0.1 g by vacuum drying. Any of the cobalt (II) phthalocyanine tetracarboxylic acid used in the following Examples was obtained by such synthesis.

Example 1

In the present Example, detection of a DNA forming an antiparallel G-quadruplex present in a solution was attempted using an anionic planar phthalocyanine. For this purpose, a solution including a DNA forming an antiparallel G-quadruplex was first prepared by the following procedure.

<Preparation of Solution Including Antiparallel G-Quadruplex-Forming DNA>

First, a 50 mM HEPES, 100 mM NaCl solution, pH 7 (total volume: 100 µl) including a single stranded DNA consisting of a 5'-gggttagggttagggttaggg-3' sequence (SEQ ID NO: 3) was prepared. This sequence was similar to the sequence of a human telomeric DNA, which DNA is thus referred to hereinafter as "human telomeric DNA". In this step, the concentrations of the human telomeric DNA included in this solution provided were 0.5, 2, 5, 10, 25, 50, and 100 µM, respectively. A 50 mM HEPES, 100 mM NaCl solution, pH 7 not including the DNA was also prepared as a negative control.

Next, after these solutions were incubated at 90° C. for 5 min, they were cooled to 0° C. at a cooling speed of 2° C./min, and finally incubated at 0° C. for 2 hrs (hereinafter, when the term of "annealing" or "annealing treatment" is described, it refers to this series of temperature control, unless otherwise stated particularly).

Subsequently, in order to confirm formation of the antiparallel G-quadruplex from the human telomeric DNA in each solution obtained by the process described above, the CD analysis was performed on each solution. As a result, a positive peak at around 295 nm, and a negative peak at around 265 nm were observed on any of the solutions except for the negative control solution, as shown in FIG. 17. This finding suggests that an antiparallel G-quadruplex was formed.

In addition, absolute values of the positive and negative peaks were the greatest for the solution having the concentration of the human telomeric DNA of 100 μM, and the values for other solutions decreased in the descending order of from 50, 25, 10, 5, 2, to 0.5 μM. This suggests that when the concentration of the human telomeric DNA included initially is higher, the concentration of the resulting antiparallel G-quadruplex-forming DNA is also higher.

Hereinafter, solutions obtained by subjecting the solutions having the concentration of the human telomeric DNA of 100, 50, 25, 10, 5, 2 and 0.5 μM to the aforementioned series of annealing treatment are referred to as, respectively, anti-G-quadruplex solutions A, B, C, D, E, F and G. Meanwhile, a solution obtained by subjecting the solution not including the DNA prepared as a negative control to the aforementioned series of annealing treatment is referred to as a NC solution.

Next, using the Anti-G-quadruplex solutions A, B, C, D, E, F and G, and the NC solution obtained by the steps described above, an experiment for the detection of an antiparallel G-quadruplex with an anionic phthalocyanine was carried out. The method for the experiment is as in the following.

<Detection with Anionic Copper Phthalocyanine>

First, a 50 mM HEPES, 100 mM NaCl solution, pH 7 (total volume: 20 μl) including 15 μM Copper (II) phthalocyanine-3,4',4'',4'''-tetrasulfonic acid tetrasodium salt (anionic planar phthalocyanine having copper as a coordination metal, and having a sodium salt of a sulfo group as a functional group) was prepared. Next, this phthalocyanine solution was mixed with each of the aforementioned Anti-G-quadruplex solutions C, D, E and F, and the NC solution, and the absorbance at 480 to 800 nm was measured on the liquid mixtures.

The results of measurement are shown in FIG. 18 (A). It is shown that a peak appeared in around the range of 640 to 720 nm except for the case of the NC solution not including any DNA. In addition, this peak has been proven to be greater in the order of the Anti-G-quadruplex solutions C>D>E>F. From the foregoing results, it was revealed that detection of the antiparallel G-quadruplex-forming DNA in the solution is enabled by using the Copper (II) phthalocyanine-3,4',4'',4'''-tetrasulfonic acid tetrasodium salt.

Furthermore, the relationship between the absorbance values at 691.5 nm in each graph derived from FIG. 18 (A) with the concentration of the human telomeric DNA of the sample is shown in FIG. 18 (B). This reveals high correlation between both values. Therefore, it is proven that the concentration of the single stranded DNA forming the antiparallel G-quadruplex can be quantitatively detected by using the Copper (II) phthalocyanine-3,4',4'',4'''-tetrasulfonic acid tetrasodium salt.

In addition, FIG. 18 (B) shows results of changing the structure of the human telomeric DNA included in the sample solution as described above into the antiparallel G-quadruplex by annealing, followed by addition of the Copper (II) phthalocyanine-3,4',4'',4'''-tetrasulfonic acid tetrasodium salt. Also in the case in which the Copper (II) phthalocyanine-3,4',4'',4'''-tetrasulfonic acid tetrasodium salt was added before the annealing treatment (i.e., in the case of process shown in FIG. 10 (A)), high correlation between the obtained absorbance value at 691.5 nm and the concentration of the human telomeric DNA of the sample was found similarly to the case shown in FIG. 18 (B).

<Detection with Anionic Nickel Phthalocyanine>

First, a 50 mM HEPES, 100 mM NaCl solution, pH 7 (total volume: 20 μl) including 15 μM Nickel (II) phthalocyanine tetrasulfonic acid tetrasodium salt (anionic planar phthalocyanine having nickel as a coordination metal, and having a sodium salt of a sulfo group as a functional group) was prepared. Next, this phthalocyanine solution was mixed with each of the aforementioned Anti-G-quadruplex solutions D, E, F and G, and the NC solution, followed by measurement of the absorbance at 480 to 800 nm on the liquid mixtures.

The results of measurement are shown in FIG. 19 (A). It is shown that a peak appeared in around the range of 640 to 720 nm except for the case of the NC solution not including any DNA. In addition, this peak has been proven to be greater in the order of the Anti-G-quadruplex solutions D>E>F>G. From the foregoing results, it was revealed that detection of the antiparallel G-quadruplex-forming DNA in the solution is enabled by using the Nickel (II) phthalocyanine tetrasulfonic acid tetrasodium salt.

Furthermore, the relationship between the absorbance values at 691.5 nm in each graph derived from FIG. 19 (A) with the concentration of the human telomeric DNA of the sample is shown in FIG. 19 (B). This reveals high correlation between both values. Therefore, it is proven that the concentration of the single stranded DNA forming the antiparallel G-quadruplex can be quantitatively detected by using the Nickel (II) phthalocyanine tetrasulfonic acid tetrasodium salt.

In addition, FIG. 19 (B) shows results of changing the structure of the human telomeric DNA included in the sample solution as described above into the antiparallel G-quadruplex by annealing, followed by addition of the Nickel (II) phthalocyanine tetrasulfonic acid tetrasodium salt. Also in the case in which the Nickel (II) phthalocyanine tetrasulfonic acid tetrasodium salt was added before the annealing treatment (i.e., in the case of process shown in FIG. 10 (A)), high correlation between the obtained absorbance value at 691.5 nm and the concentration of the human telomeric DNA of the sample was found similarly to the case shown in FIG. 19 (B).

<Detection with Anionic Phthalocyanine not Having a Coordination Metal>

First, a 50 mM HEPES, 100 mM NaCl solution, pH 7 (total volume: 20 μl) including 15 μM Phthalocyanine tetrasulfonic acid (anionic planar phthalocyanine not having a coordination metal, and having a sulfo group as a functional group) was prepared.

Next, this phthalocyanine solution was mixed with each of the aforementioned Anti-G-quadruplex solutions D, E, F and G, and the NC solution, and the absorbance at 480 to 800 nm was measured on the liquid mixtures. The results of measurement are shown in FIG. 20 (A). It is shown that two peaks appeared in the range of 660 to 740 nm except for the case of the NC solution not including any DNA. In addition, this peak has been proven to be greater in the order of the Anti-G-quadruplex solutions D>E>F>G. From the foregoing results, it was revealed that detection of the antiparallel G-quadruplex-forming DNA in the solution is enabled by using the Phthalocyanine tetrasulfonic acid.

Furthermore, the relationship between the absorbance values at 677.5 nm in each graph derived from FIG. 20 (A) with the concentration of the human telomeric DNA of the sample is shown in FIG. 20 (B), and the relationship between the absorbance value at 710.0 nm and the concentration of the human telomeric DNA of the sample is shown in FIG. 20 (C). These reveal high correlation between both values. Therefore, it is proven that the concentration of the single stranded DNA forming the antiparallel G-quadruplex can be quantitatively detected by using the Phthalocyanine tetrasulfonic acid.

In addition, FIG. 20 (B) and FIG. 20 (C) show results of changing the structure of the human telomeric DNA included in the sample solution as described above into the antiparallel G-quadruplex by annealing, followed by addition of the Phthalocyanine tetrasulfonic acid. Also in the case in which the Phthalocyanine tetrasulfonic acid was added before the annealing treatment (i.e., in the case of process shown in FIG. 10 (A)), high correlation between the obtained absorbance values at 677.5 nm and 710.0 nm and the concentrations of the human telomeric DNA of the sample was found similarly to the case shown in FIG. 20 (B) and FIG. 20 (C).

<Detection with Anionic Cobalt Phthalocyanine>

First, a 50 mM HEPES, 100 mM NaCl solution, pH 7 (total volume: 20 µl) including 15 µM Cobalt (II) phthalocyanine tetracarboxylic acid (anionic planar phthalocyanine having cobalt as a coordination metal, and having a carboxyl group as a functional group) was prepared. Next, this phthalocyanine solution was mixed with each of the aforementioned Anti-G-quadruplex solutions B, C, D and G, and the NC solution, and the absorbance at 480 to 800 nm was measured on the liquid mixtures.

The results of measurement are shown in FIG. 33 (A). It is shown that a peak appeared in around the range of 640 to 720 nm except for the case of the NC solution not including any DNA. In addition, this peak has been proven to be greater in the order of the Anti-G-quadruplex solutions B>C>D>G. From the foregoing results, it was revealed that detection of the antiparallel G-quadruplex-forming DNA in the solution is enabled by using the Cobalt (II) phthalocyanine tetracarboxylic acid.

Furthermore, the relationship between the absorbance values at 684.5 nm in each graph derived from FIG. 33 (A) with the concentration of the human telomeric DNA of the sample is shown in FIG. 33 (B). This reveals high correlation between both values. Therefore, it is proven that the concentration of the single stranded DNA forming the antiparallel G-quadruplex can be quantitatively detected by using the Cobalt (II) phthalocyanine tetracarboxylic acid. In addition, FIG. 33 (B) shows results of changing the structure of the human telomeric DNA included in the sample solution as described above into the antiparallel G-quadruplex by annealing, followed by addition of the Cobalt (II) phthalocyanine tetracarboxylic acid. Also in the case in which the Cobalt (II) phthalocyanine tetracarboxylic acid was added before the annealing treatment (i.e., in the case of process shown in FIG. 10 (A)), high correlation between the obtained absorbance value at 684.5 nm and the concentration of the human telomeric DNA of the sample was found similarly to the case shown in FIG. 33 (B).

Meanwhile, elevation of the peak in the range of 640 to 720 nm found when the Cobalt (II) phthalocyanine tetracarboxylic acid was used was less than that in the case in which the Copper (II) phthalocyanine-3,4',4",4'''-tetrasulfonic acid tetrasodium salt, the Nickel (II) phthalocyanine tetrasulfonic acid tetrasodium salt or the Phthalocyanine tetrasulfonic acid was used. This event is presumed to result from insufficient purification of the synthesized Cobalt (II) phthalocyanine tetracarboxylic acid.

<Detection with Anionic Iron Phthalocyanine>

First, a 50 mM HEPES, 100 mM NaCl solution, pH 7 (total volume: 20 µl) including 15 µM Iron (III) phthalocyanine-4, 4',4",4'''-tetrasulfonic acid, compound with oxygen monosodium salt hydrate (anionic phthalocyanine having iron as a coordination metal, and having a sulfo group as a functional group) was prepared. Next, this phthalocyanine solution was mixed with each of the aforementioned Anti-G-quadruplex solution B, and the NC solution, and the absorbance at 480 to 800 nm was measured on the liquid mixtures.

The results of measurement are shown in FIG. 21. It is shown that the case in which the Anti-G-quadruplex solution B was used yielded almost the same results as those in the case in which the NC solution not including any DNA was used. From the foregoing results, it was revealed that the antiparallel G-quadruplex-forming DNA in the solution cannot be detected even though the Iron (III) phthalocyanine-4, 4',4",4'''-tetrasulfonic acid, compound with oxygen monosodium salt hydrate was used.

In addition to the phthalocyanines described above, a similar experiment was carried out on Zinc (II) phthalocyanine tetrasulfonic acid (anionic planar phthalocyanine having zinc as a coordination metal, and having a sulfo group as a functional group), and as a result, a peak was observed in the range of 640 to 740 nm only in the case in which an Anti-G-quadruplex solution was mixed.

Therefore, results of Example 1 revealed that an antiparallel G-quadruplex can be detected when any of the anionic planar phthalocyanine was used, except for the case in which the anionic iron phthalocyanine was used. In addition, also in the case in which the Zinc (II) phthalocyanine tetrasulfonic acid was used, high correlation between the absorbance value at a specified wavelength in the aforementioned peak range and the concentration of the human telomeric DNA in the sample was found.

Therefore, from the results of Example 1 in the foregoing, it is proven that the concentration of the single stranded DNA forming the antiparallel G-quadruplex present in the sample solution can be quantitatively detected when any of the anionic phthalocyanine was used, except for the case in which the anionic iron phthalocyanine was used.

Example 2

In the present Example, detection of a DNA forming an antiparallel G-quadruplex and a DNA forming a parallel G-quadruplex coexisting in a solution was attempted using an anionic phthalocyanine. For this purpose, a coexisting solution of a DNA forming an antiparallel G-quadruplex and a DNA forming a parallel G-quadruplex was first prepared by the following procedure.

<Preparation of Solution of Coexisting Antiparallel G-Quadruplex-Forming DNA and Parallel G-Quadruplex-Forming DNA>

First, a 50 mM HEPES, 100 mM KCl solution, pH 7 (total volume: 100 µl) including a human telomeric DNA was prepared. In this step, the concentrations of the human telomeric DNA included in this solution provided were 1, 2, 10, 25, 50 and 100 µM, respectively. A 50 mM HEPES, 100 mM KCl solution, pH 7 not including the DNA was also prepared as a negative control. Then, these solutions were subjected to an annealing treatment.

Subsequently, in order to confirm formation of the parallel G-quadruplex from the human telomeric DNA in each solution obtained by the process described above, the CD analysis was performed on each solution. The results are shown in FIG. 12.

As explained also in connection with Example 1, it has been known that a positive peak at around 295 nm, and a negative peak at around 265 nm are observed in the results of the CD measurement in the case of the antiparallel G-quadruplex. To the contrary, in the case of the parallel G-quadruplex, it has been known that a positive peak at around 260 nm, and a negative peak at around 240 nm are observed. On the basis of these findings, the results of the CD measurement shown in FIG. 12 suggest coexistence of the parallel G-quadruplex and the antiparallel G-quadruplex since a negative peak at around 240 nm, and a positive peak at around 295 nm existed except for the case of the negative control solution.

In addition, with respect to any of the positive peak at around 295 nm, and the negative peak at around 240 nm, their absolute values are greater as the concentration of the human telomeric DNA are higher. This suggests that when the concentration of the human telomeric DNA included initially is higher, both the concentrations of the parallel G-quadruplex-forming DNA and the antiparallel G-quadruplex-forming DNA in the solution obtained following the annealing treatment are also higher.

Hereinafter, solutions obtained by subjecting the solutions having the concentration of the human telomeric DNA of 100, 50, 25, 10, 2 and 1 µM to the aforementioned annealing treatment are referred to as, respectively, Anti-Para-G-quadruplex solutions A, B, C, D, E and F. Meanwhile, a solution obtained by subjecting the solution not including the DNA prepared as a negative control to the aforementioned annealing treatment is referred to as a NC-2 solution.

Next, using the Anti-Para-G-quadruplex solutions A, B, C, D, E and F, and the NC-2 solution obtained by the steps described above, an experiment for the detection of a parallel G-quadruplex with an anionic phthalocyanine was carried out. The method for the experiment is as in the following.

<Detection with Anionic Copper Phthalocyanine>

First, a 50 mM HEPES, 100 mM KCl solution, pH 7 (total volume: 20 µl) including 15 µM Copper (II) phthalocyanine-3,4',4",4"'-tetrasulfonic acid tetrasodium salt was prepared. Next, this phthalocyanine solution was mixed with each of the aforementioned Anti-Para-G-quadruplex solutions B, C, D and F, and the NC-2 solution, and the absorbance at 480 to 800 nm was measured on the liquid mixtures.

The results of measurement are shown in FIG. 13 (A). It is shown that a peak appeared in around the range of 640 to 720 nm except for the case of the NC-2 solution not including any DNA. In addition, this peak has been proven to be greater in the order of the Anti-Para-G-quadruplex solutions B>C>D>F.

From the foregoing results, it was revealed that detection of the antiparallel G-quadruplex-forming DNA and parallel G-quadruplex-forming DNAs coexisting in the solution is enabled by using the Copper (II) phthalocyanine-3,4',4",4"'-tetrasulfonic acid tetrasodium salt.

Furthermore, the relationship between the absorbance values at 689.5 nm in each graph derived from FIG. 13 (A) with the concentration of the human telomeric DNA of the sample is shown in FIG. 13 (B). This reveals high correlation between both values. Therefore, it is proven that the concentrations of the single stranded DNA forming the antiparallel G-quadruplex and the single stranded DNA forming the parallel G-quadruplex can be quantitatively detected by using the Copper (II) phthalocyanine-3,4',4",4"'-tetrasulfonic acid tetrasodium salt.

In addition, FIG. 13 (B) shows results of changing the structure of the human telomeric DNA included in the sample solution as described above into the antiparallel and parallel G-quadruplexes by annealing, followed by addition of the Copper (II) phthalocyanine-3,4',4",4"'-tetrasulfonic acid tetrasodium salt. However, also in the case in which the Copper (II) phthalocyanine-3,4',4",4"'-tetrasulfonic acid tetrasodium salt was added before the annealing treatment, high correlation between the obtained absorbance value at 689.5 nm and the concentration of the human telomeric DNA of the sample was found similarly to the case shown in FIG. 13 (B).

<Detection with Anionic Nickel Phthalocyanine>

First, a 50 mM HEPES, 100 mM KCl solution, pH 7 (total volume: 20 µl) including 15 µM Nickel (II) phthalocyanine tetrasulfonic acid tetrasodium salt was prepared. Next, this phthalocyanine solution was mixed with each of the aforementioned Anti-Para-G-quadruplex solutions A, B, C and E, and the NC-2 solution, followed by measurement of the absorbance at 480 to 800 nm on the liquid mixtures.

The results of measurement are shown in FIG. 14 (A). It is shown that a peak appeared in around the range of 640 to 720 nm except for the case of the NC-2 solution not including any DNA. In addition, this peak has been proven to be greater in the order of the Anti-Para-G-quadruplex solutions A>B>C>E. From the foregoing results, it was revealed that detection of the antiparallel G-quadruplex-forming DNA and parallel G-quadruplex-forming DNA coexisting in the solution is enabled by using the Nickel (II) phthalocyanine tetrasulfonic acid tetrasodium salt.

Furthermore, the relationship between the absorbance values at 677.5 nm in each graph derived from FIG. 14 (A) with the concentration of the human telomeric DNA of the sample is shown in FIG. 14 (B). This reveals high correlation between both values. Therefore, it is proven that the concentrations of the single stranded DNAs forming the antiparallel G-quadruplex and the single stranded DNA forming the parallel G-quadruplex can be quantitatively detected by using the Nickel (II) phthalocyanine tetrasulfonic acid tetrasodium salt.

In addition, FIG. 14 (B) shows results of changing the structure of the human telomeric DNA included in the sample solution as described above into the antiparallel and parallel G-quadruplexes by annealing, followed by addition of the Nickel (II) phthalocyanine tetrasulfonic acid tetrasodium salt. However, also in the case in which the Nickel (II) phthalocyanine tetrasulfonic acid tetrasodium salt was added before the annealing treatment, high correlation between the obtained absorbance value at 677.5 nm and the concentration of the human telomeric DNA of the sample was found similarly to the case shown in FIG. 14 (B).

<Detection with Anionic Phthalocyanine not Having a Coordination Metal>

First, a 50 mM HEPES, 100 mM KCl solution, pH 7 (total volume: 20 µl) including 15 µM Phthalocyanine tetrasulfonic acid was prepared. Next, this phthalocyanine solution was mixed with each of the aforementioned Anti-Para-G-quadruplex solutions B, C, D and F, and the NC-2 solution, and the absorbance at 480 to 800 nm was measured on the liquid mixtures.

The results of measurement are shown in FIG. 15 (A). It is shown that two peaks appeared in the range of 660 to 740 nm except for the case of the NC-2 solution not including any DNA. In addition, this peak has been proven to be greater in the order of the Anti-Para-G-quadruplex solutions B>C>D>F. From the foregoing results, it was revealed that detection of the antiparallel G-quadruplex-forming DNA and the parallel G-quadruplex-forming DNA coexisting in the solution is enabled by using the Phthalocyanine tetrasulfonic acid.

Furthermore, the relationship between the absorbance values at 708.0 nm in each graph derived from FIG. 15 (A) with the concentration of the human telomeric DNA of the sample is shown in FIG. 15 (B), and the relationship between the absorbance value at 675.0 nm and the concentration of the human telomeric DNA of the sample is shown in FIG. 15 (C). These reveal high correlation between both values. Therefore, it is proven that the concentration of the single stranded DNA forming the antiparallel G-quadruplex-forming DNA and the single stranded DNA forming the parallel G-quadruplex can be quantitatively detected by using the Phthalocyanine tetrasulfonic acid.

In addition, FIG. 15 (B) and FIG. 15 (C) show results of changing the structure of the human telomeric DNA included in the sample solution as described above into the antiparallel and parallel G-quadruplexes by annealing, followed by addition of the Phthalocyanine tetrasulfonic acid. However, also in the case in which the Phthalocyanine tetrasulfonic acid was added before the annealing treatment, high correlation between the obtained absorbance values at 708.0 nm and 675.0 nm and the concentrations of the human telomeric DNA of the sample was found similarly to the case shown in FIG. 15 (B) and FIG. 15 (C).

<Detection with Anionic Cobalt Phthalocyanine>

First, a 50 mM HEPES, 100 mM KCl solution, pH 7 (total volume: 20 µl) including 15 µM Cobalt (II) phthalocyanine tetracarboxylic acid was prepared. Next, this phthalocyanine solution was mixed with each of the aforementioned Anti-Para-G-quadruplex solutions B, C, D and E, and the NC-2 solution, and the absorbance at 480 to 800 nm was measured on the liquid mixtures.

The results of measurement are shown in FIG. 34 (A). It is shown that a peak appeared in around the range of 640 to 720 nm except for the case of the NC-2 solution not including any DNA. In addition, this peak has been proven to be greater in the order of the Anti-Para-G-quadruplex solutions B>C>D>E.

From the foregoing results, it was revealed that detection of the antiparallel G-quadruplex-forming DNA and the parallel G-quadruplex-forming DNA coexisting in the solution is enabled by using the Cobalt (II) phthalocyanine tetracarboxylic acid.

Furthermore, the relationship between the absorbance values at 679.0 nm in each graph derived from FIG. 34 (A) with the concentration of the human telomeric DNA of the sample is shown in FIG. 34 (B). This reveals high correlation between both values. Therefore, it is proven that the concentration of the single stranded DNA forming the antiparallel G-quadruplex and the single stranded DNA forming the parallel G-quadruplex can be quantitatively detected by using the Cobalt (II) phthalocyanine tetracarboxylic acid.

In addition, FIG. 34 (B) shows results of changing the structure of the human telomeric DNA included in the sample solution as described above into the antiparallel and parallel G-quadruplexes by annealing, followed by addition of the Cobalt (II) phthalocyanine tetracarboxylic acid. However, also in the case in which the Cobalt (II) phthalocyanine tetracarboxylic acid was added before the annealing treatment, high correlation between the obtained absorbance value at 679.0 nm and the concentration of the human telomeric DNA of the sample was found similarly to the case shown in FIG. 34 (B).

Meanwhile, elevation of the peak in the range of 640 to 720 nm found when the Cobalt (II) phthalocyanine tetracarboxylic acid was used was less than that in the case in which the Copper (II) phthalocyanine-3,4',4",4'"-tetrasulfonic acid tetrasodium salt, the Nickel (II) phthalocyanine tetrasulfonic acid tetrasodium salt or the Phthalocyanine tetrasulfonic acid was used. This event is presumed to result from insufficient purification of the synthesized Cobalt (II) phthalocyanine tetracarboxylic acid.

<Detection with Anionic Iron Phthalocyanine>

First, a 50 mM HEPES, 100 mM KCl solution, pH 7 (total volume: 20 µl) including 15 µM Iron (III) phthalocyanine-4,4',4",4'"-tetrasulfonic acid, compound with oxygen monosodium salt hydrate was prepared. Next, this phthalocyanine solution was mixed with each of the aforementioned Anti-Para-G-quadruplex solution B, and the NC-2 solution, and the absorbance at 480 to 800 nm was measured on the liquid mixtures.

The results of measurement are shown in FIG. 16. It is shown that the results obtained in both cases of the Anti-Para-G-quadruplex solution B and the NC-2 solution were almost the same. Accordingly, it was revealed that the antiparallel G-quadruplex-forming DNA and the parallel G-quadruplex-forming DNA coexisting in the solution cannot be detected when the Iron (III) phthalocyanine-4,4',4",4'"-tetrasulfonic acid, compound with oxygen monosodium salt hydrate was used.

In addition to the phthalocyanines described above, a similar experiment was carried out using Zinc (II) phthalocyanine tetrasulfonic acid (anionic planar phthalocyanine having a sulfo group as a functional group, and having zinc as a coordination metal), and as a result, a peak was observed in the range of 640 to 740 nm only in the case in which an Anti-Para-G-quadruplex solution was mixed. Therefore, the results set forth above revealed that the antiparallel G-quadruplex and the parallel G-quadruplex coexisting in a solution can be detected when any of the anionic phthalocyanine was used, except for the case in which the anionic iron phthalocyanine was used.

In addition, also in the case in which the Zinc (II) phthalocyanine tetrasulfonic acid was used, high correlation between the absorbance value at a specified wavelength in the aforementioned peak range and the concentration of the human telomeric DNA in the sample was found. Therefore, it was proven that the concentration of the single stranded DNA forming the antiparallel G-quadruplex and the single stranded DNA forming the parallel G-quadruplex present in the sample solution can be quantitatively detected even when the Zinc (II) phthalocyanine tetrasulfonic acid was used.

Example 3

From the results of the aforementioned Example 1 and Example 2, it is proven that a G-quadruplex can be detected irrespective of being either parallel or antiparallel, using any anionic phthalocyanine other than anionic iron phthalocyanine. In the present Example 3, in order to ascertain the specificity of the anionic phthalocyanine for G-quadruplexes, experiments for detecting a single stranded DNA and a double stranded DNA using an anionic phthalocyanine were carried out. To this end, a solution including a single stranded DNA, and a solution including a double stranded DNA were first prepared by the following procedure.

<Preparation of Solution Including Single Stranded DNA>

First, a 50 mM HEPES, 100 mM NaCl solution, pH 7 (total volume: 100 µl) including a single stranded DNA consisting of a sequence of 5'-ttttttttttttttttttttt-3' (SEQ ID NO: 4) at a concentration of 50 µM was prepared, and the solution was then incubated at 90° C. for 5 min. After cooling to 0° C. at a cooling speed of 2° C./min, the solution was finally incubated at 0° C. for 2 hours. The DNA in thus resulting solution remains a single stranded DNA also following the incubation (hereinafter, this solution being referred to as single stranded DNA solution).

<Preparation of Solution Including Double Stranded DNA>

First, a 50 mM HEPES, 100 mM NaCl solution, pH 7 (total volume: 100 µl) including a single stranded DNA consisting of a sequence of 5'-AGAAGAGAAAGA-3' (SEQ ID NO: 5) and a single stranded DNA consisting of a sequence of 5'-TCTTTCTCTTCT-3' (antisense strand of SEQ ID NO: 5)

at a concentration of 50 µM, respectively, was prepared, and the solution was then incubated at 90° C. for 5 min. After cooling to 0° C. at a cooling speed of 2° C./min, the solution was finally incubated at 0° C. for 2 hours. Since the above two kinds of DNAs are complementary to one another, both DNAs will form a double stranded DNA in the solution as a result of the incubation (hereinafter, this solution being referred to as double stranded DNA solution).

Using the single stranded DNA solution and the double stranded DNA solution obtained in the steps described above, experiments for detecting single stranded and double stranded DNAs with anionic phthalocyanine were carried out. The method for the experiment is as in the following.

<Detection with Anionic Copper Phthalocyanine>

First, a 50 mM HEPES, 100 mM NaCl solution, pH 7 (total volume: 20 µl) including 15 µM Copper (II) phthalocyanine-3,4',4'',4'''-tetrasulfonic acid tetrasodium salt was prepared. Next, this phthalocyanine solution was mixed with each of the single stranded DNA solution and the double stranded DNA solution, and the absorbance at 480 to 800 nm was measured on the liquid mixtures. Results of the measurement on each of the single stranded DNA solution and the double stranded DNA solution are shown in FIG. 22 (A) and FIG. 22 (B).

In each diagram, results obtained using the NC solution in Example 1 are shown together with as a negative control. These reveal that in both cases of the single stranded DNA solution and the double stranded DNA solution, results almost comparative to the case in which the NC solution was used were achieved in spite of the state including the DNA at a concentration as high as 50 µM. Therefore, from the foregoing results and results of Example and Example 2, it was revealed that detection of the G-quadruplex-forming DNA using the Copper (II) phthalocyanine-3,4',4'',4'''-tetrasulfonic acid tetrasodium salt is extremely highly specific.

<Detection with Anionic Nickel Phthalocyanine>

First, a 50 mM HEPES, 100 mM NaCl solution, pH 7 (total volume: 20 µl) including 15 µM Nickel (II) phthalocyanine tetrasulfonic acid tetrasodium salt was prepared. Next, this phthalocyanine solution was mixed with each of the single stranded DNA solution and the double stranded DNA solution, and the absorbance at 480 to 800 nm was measured on the liquid mixtures. Results of the measurement on each of the single stranded DNA solution and the double stranded DNA solution are shown in FIG. 23 (A) and FIG. 23 (B). In each diagram, results obtained using the NC solution in Example 1 are shown together with as a negative control.

These reveal that in both cases of the single stranded DNA solution and the double stranded DNA solution, results almost comparative to the case in which the NC solution was used were achieved in spite of the state including the DNA at a concentration as high as 50 µM. Therefore, from the foregoing results and results of Example 1 and Example 2, it was revealed that detection of the G-quadruplex-forming DNA using the Nickel (II) phthalocyanine tetrasulfonic acid tetrasodium salt is extremely highly specific.

<Detection with Anionic Phthalocyanine not Having a Coordination Metal>

First, a 50 mM HEPES, 100 mM NaCl solution, pH 7 (total volume: 20 µl) including 15 µM Phthalocyanine tetrasulfonic acid was prepared. Next, this phthalocyanine solution was mixed with each of the single stranded DNA solution and the double stranded DNA solution, and the absorbance at 480 to 800 nm was measured on the liquid mixtures. Results of the measurement on each of the single stranded DNA solution and the double stranded DNA solution are shown in FIG. 24 (A) and FIG. 24 (B).

In each diagram, results obtained using the NC solution in Example 1 are shown together with as a negative control. These reveal that in both cases of the single stranded DNA solution and the double stranded DNA solution, results almost comparative to the case in which the NC solution was used were achieved in spite of the state including the DNA at a concentration as high as 50 µM. Therefore, from the foregoing results and results of Example and Example 2, it was revealed that detection of the G-quadruplex-forming DNA using the Phthalocyanine tetrasulfonic acid is extremely highly specific.

<Detection with Anionic Cobalt Phthalocyanine>

First, a 50 mM HEPES, 100 mM NaCl solution, pH 7 (total volume: 20 µl) including 15 µM Cobalt (II) phthalocyanine tetracarboxylic acid was prepared. Next, this phthalocyanine solution was mixed with each of the single stranded DNA solution and the double stranded DNA solution, and the absorbance at 480 to 800 nm was measured on the liquid mixtures. Results of the measurement on each of the single stranded DNA solution and the double stranded DNA solution are shown in FIG. 35 (A) and FIG. 35 (B). In each diagram, results obtained using the NC solution in Example 1 are shown together with as a negative control.

These reveal that in both cases of the single stranded DNA solution and the double stranded DNA solution, results almost comparative to the case in which the NC solution was used were achieved in spite of the state including the DNA at a concentration as high as 50 µM. Therefore, from the foregoing results and results of Example 1 and Example 2, it was revealed that detection of the G-quadruplex-forming DNA using the Cobalt (II) phthalocyanine tetracarboxylic acid is extremely highly specific.

In addition to the foregoing phthalocyanines, as a result of a similar experiment carried out using Zinc (II) phthalocyanine tetrasulfonic acid (anionic phthalocyanine having a sulfo group as a functional group, and having zinc as a coordination metal), results almost comparative to the case in which the NC solution was used were achieved in spite of the state including the DNA at a concentration as high as 50 µM, in both cases of the single stranded DNA solution and the double stranded DNA solution.

Example 4

In the aforementioned Example 1 and Example 2, a single stranded DNA having a sequence identical to a sequence of human telomeric DNA was used to prepare a parallel or antiparallel G-quadruplex DNA, whereby possible detection of the G-quadruplex DANs with an anionic phthalocyanine other than those having iron as a coordination metal, or possible quantitative detection of the aforementioned single stranded DNA on the basis of the detection results as described above were demonstrated. In the present Example 4, it was verified as to whether the aforementioned results of Example 1 and Example 2 are limited to the G-quadruplex having a sequence of human telomeric DNA, or similar results can be obtained for G-quadruplexes having a sequence other than human telomeric DNA.

<Detection of Parallel G-Quadruplex-Forming DNA Consisting of a Sequence of 5'-ggggttttgggg-3' (SEQ ID NO: 6), with Anionic Copper Phthalocyanine>

First, a solution including a single stranded DNA consisting of a sequence of 5'-ggggttttgggg-3' (SEQ ID NO: 6) (hereinafter, referred to as G4T4G4 DNA), 2.5 µM Copper (II) phthalocyanine-3,4',4'',4'''-tetrasulfonic acid tetrasodium salt, 50 mM HEPES, and 100 mM KCl, pH 7 was prepared (total volume: 100 µl). The G4T4G4 DNA sequence has been known to have a different sequence from that of human telomeric DNA, but forms a parallel G-quadruplex through an annealing treatment in the presence of K. With respect to the aforementioned solution, those having a G4T4G4 DNA concentration of 0, 1, 2, 3, 4, 5 and 10 µM, respectively were prepared.

Next, these solutions were subjected to an annealing treatment, and the absorbance at 480 to 800 nm was measured on these solutions. The measurement results are shown in FIG. 25 (A). Accordingly, it is apparent that a peak appears in the range of around 640 to 720 nm except for the case in which the G4T4G4 DNA was included at a concentration of 0 µM.

From the results described above, it is revealed that a parallel G-quadruplex-forming DNA consisting of the G4T4G4 DNA can be detected by using the Copper (II) phthalocyanine-3,4',4",4"'-tetrasulfonic acid tetrasodium salt.

Furthermore, the relationship between the absorbance value at 687 nm in each graph obtained in FIG. 25 (A) with the concentration of the G4T4G4 DNA in the same sample is shown in FIG. 25 (B). Accordingly, it is revealed that both values are highly correlated. Therefore, from these results, it is proven that the concentration of a G4T4G4 DNA can be quantitatively detected by using the Copper (II) phthalocyanine-3,4',4",4"'-tetrasulfonic acid tetrasodium salt.

<Detection of Parallel G-Quadruplex-Forming DNA Consisting of a Sequence of 5'-ggggttttgggg-3' (SEQ ID NO: 6), with Anionic Nickel Phthalocyanine>

In a Similar manner to the above "Detection of Parallel G-quadruplex-forming DNA consisting of a sequence of 5'-ggggttttgggg-3' (SEQ ID NO: 6), with Anionic Copper Phthalocyanine", an experiment was carried out using Nickel (II) phthalocyanine tetrasulfonic acid, tetrasodium salt in place of the Copper (II) phthalocyanine-3,4',4",4"'-tetrasulfonic acid tetrasodium salt. Also, the G4T4G4 DNA concentrations employed were 0, 1, 2, 3, 4, 5, 10 and 25 µM. The results are shown in FIG. 26 (A). Accordingly, it is apparent that a peak appears in the range of around 640 to 720 nm except for the case in which the G4T4G4 DNA was at 0 µM.

From the results described above, it is revealed that a parallel G-quadruplex-forming DNA consisting of the G4T4G4 DNA can be detected using the Nickel (II) phthalocyanine tetrasulfonic acid, tetrasodium salt.

Furthermore, the relationship between the absorbance value at 677.5 nm in each graph obtained in FIG. 26 (A) with the concentration of the G4T4G4 DNA in the same sample is shown in FIG. 26 (B). Accordingly, it is revealed that both values are highly correlated. Therefore, from these results, it is proven that the concentration of a G4T4G4 DNA can be quantitatively detected by using the Nickel (II) phthalocyanine tetrasulfonic acid tetrasodium salt.

<Detection of Parallel G-Quadruplex-Forming DNA Consisting of a Sequence of 5'-ggggttttgggg-3' (SEQ ID NO: 6), with Anionic Phthalocyanine not Having Coordination Metal>

In a Similar manner to the above "Detection of Parallel G-quadruplex-forming DNA consisting of a sequence of 5'-ggggttttgggg-3' (SEQ ID NO: 6), with Anionic Copper Phthalocyanine", an experiment was carried out using Phthalocyanine tetrasulfonic acid in place of the Copper (II) phthalocyanine-3,4',4",4"'-tetrasulfonic acid tetrasodium salt. Also, the G4T4G4 DNA concentrations employed were 0, 1, 2, 10 and 25 µM. The results are shown in FIG. 27 (A). Accordingly, it is apparent that two peak appear in the range of around 660 to 740 nm except for the case in which the G4T4G4 DNA was at 0 µM.

From the results described above, it is revealed that a parallel G-quadruplex-forming DNA consisting of the G4T4G4 DNA can be detected by using the Phthalocyanine tetrasulfonic acid.

Furthermore, the relationship between the absorbance value at 705.0 nm in each graph obtained in FIG. 27 (A) with the concentration of the G4T4G4 DNA thereof is shown in FIG. 27 (B); and the relationship between the absorbance value at 673.0 nm and the concentration of the human telomeric DNA of the sample is shown in FIG. 27 (C). Accordingly, it is revealed that both values are highly correlated. Therefore, from these results, it is proven that the concentration of a G4T4G4 DNA can be quantitatively detected by using the Phthalocyanine tetrasulfonic acid.

<Detection of Parallel G-Quadruplex-Forming DNA Consisting of a Sequence of 5'-ggggttttgggg-3' (SEQ ID NO: 6), with Anionic Cobalt Phthalocyanine>

In a Similar manner to the above "Detection of Parallel G-quadruplex-forming DNA consisting of a sequence of 5'-ggggttttgggg-3' (SEQ ID NO: 6), with Anionic Copper Phthalocyanine", an experiment was carried out using Cobalt (II) phthalocyanine tetracarboxylic acid in place of the Copper (II) phthalocyanine-3,4',4",4"'-tetrasulfonic acid tetrasodium salt. However, the concentration of the Cobalt (II) phthalocyanine tetracarboxylic acid was 30 µM. Also, the G4T4G4 DNA concentrations employed were 0, 5, 10, 25 and 50 µM. The results are shown in FIG. 36 (A). Accordingly, it is apparent that a peak appears in the range of around 640 to 720 nm except for the case in which the G4T4G4 DNA was included at a concentration of 0 µM.

From the results described above, it is revealed that a parallel G-quadruplex-forming DNA consisting of the G4T4G4 DNA can be detected by using the Cobalt (II) phthalocyanine tetracarboxylic acid.

Furthermore, the relationship between the absorbance value at 680 nm in each graph obtained in FIG. 36 (A) with the concentration of the G4T4G4 DNA in the same sample is shown in FIG. 36 (B). Accordingly, it is revealed that both values are highly correlated. Therefore, from these results, it is proven that the concentration of a G4T4G4 DNA can be quantitatively detected by using the Cobalt (II) phthalocyanine tetracarboxylic acid.

Meanwhile, elevation of the peak in the range of 640 to 720 nm found when the Cobalt (II) phthalocyanine tetracarboxylic acid was used was less than that in the case in which the Copper (II) phthalocyanine-3,4',4",4"'-tetrasulfonic acid tetrasodium salt, the Nickel (II) phthalocyanine tetrasulfonic acid tetrasodium salt or the Phthalocyanine tetrasulfonic acid was used. This event is presumed to result from insufficient purification of the synthesized Cobalt (II) phthalocyanine tetracarboxylic acid.

<Detection of Parallel G-Quadruplex-Forming DNA Consisting of a Sequence of 5'-ggggttttgggg-3' (SEQ ID NO: 6), with Anionic Iron Phthalocyanine>

In a Similar manner to the above "Detection of Parallel G-quadruplex-forming DNA consisting of a sequence of 5'-ggggttttgggg-3' (SEQ ID NO: 6), with Anionic Copper Phthalocyanine", an experiment was carried out using Iron (III) phthalocyanine-4,4',4",4"'-tetrasulfonic acid, compound with oxygen monosodium salt hydrate in place of the Copper (II) phthalocyanine-3,4',4",4"'-tetrasulfonic acid tetrasodium salt. Also, the G4T4G4 DNA concentrations employed were 0, 1, 2, 3, 4, 5, 10 and 25 µM.

The results are shown in FIG. 28. Accordingly, it is apparent that any of the concentrations lead the same results as in the case of the concentration of 0 µM. Therefore, it is revealed that a parallel G-quadruplex-forming DNA consisting of the G4T4G4 DNA can not be detected using the Iron (III) phthalocyanine-4,4',4'',4'''-tetrasulfonic acid, compound with oxygen monosodium salt hydrate.

In addition to the phthalocyanines described above, a similar experiment was carried out using Zinc (II) phthalocyanine tetrasulfonic acid (anionic phthalocyanine having a sulfo group as a functional group, and having zinc as a coordination metal), and as a result, a peak was observed in the range of 640 to 740 nm in any case except for the case in which the concentration of the G4T4G4 DNA was 0 μM. Therefore, the results set forth above revealed that the parallel G-quadruplex-forming DNA consisting of the G4T4G4 DNA can be detected when any of the anionic phthalocyanine was used, except for the case in which the anionic iron phthalocyanine was used.

In addition, also in the case in which the Zinc (II) phthalocyanine tetrasulfonic acid was used, high correlation between the absorbance value at a specified wavelength in the aforementioned peak range and the concentration of the G4T4G4 DNA was found. Therefore, it is proven that the concentration of the G4T4G4 DNA can be quantitatively detected even when the Zinc (II) phthalocyanine tetrasulfonic acid was used.

The results of Example 1 to Example 4 are summarized in FIG. 29 along with drawings illustrating the structure of each phthalocyanine. In FIG. 29, the symbol "○" indicates that an absorbance peak was obtained in the range of the wavelength of 640 to 740 nm depending on the presence of the target DNA, in the experiment for detecting a DNA of each Example. To the contrary, the symbol "x" indicates that such a peak was not obtained. Moreover, the symbol "–" indicates that no experiment was carried out. Accordingly, it is found that a G-quadruplex can be specifically detected with any anionic phthalocyanine except for anionic iron phthalocyanine, irrespective of the type of the anionic functional group (either sulfo group or carboxyl group), and also irrespective of the type of the coordination metal. In addition, also in connection with the type of the G-quadruplex, it is found that detection is enabled without depending on the type of either parallel or antiparallel, as long as it is a G-quadruplex set forth with reference to FIG. 2, also without limitation of the sequence, not only the human telomeric DNA sequence.

It should be noted that the following two important matters have been known in connection with phthalocyanine and G-quadruplex. First, the absorbance exhibited by the phthalocyanine should be noted. Phthalocyanines usually associate among the molecules due to stacking interaction caused from one another since its n-plane is large when dissolved in a solution. Typical UV absorption spectrum in this state is shown in FIG. 30 (A). On the other hand, when a surfactant is added to the phthalocyanine solution in this state, a peak will appear at around 640 to 740 nm (FIG. 30 (B)). This is known as a peak indicating the presence of the phthalocyanine in a dissociated state due to addition of the surfactant (in other words, the monomer state). That is, according to the results of Examples 1 to 4, other anionic phthalocyanines except for anionic iron phthalocyanine are present as a monomer at least in part when mixed with the G-quadruplex, whereby a peak at around 640 to 730 nm appears.

The second important finding relates to interaction of a G-quadruplex with other organic molecules. The G-quadruplex has a structure in which large n-planes are stacked, referred to as G-qartet face as shown in FIG. 2. In such structures, other molecules having a n-plane are likely to intercalate in between the G-qartet faces. It is therefore, reported hitherto that molecules such as, for example, cationic anthraquinones and cationic porphyrins intercalate in the G-quadruplex resulting from the effects of electrostatic interaction and stacking interaction.

Therefore, taking into consideration of these findings, the results of Example 1 to Example 4 herein suggest that the G-quadruplex is specifically detected by other anionic phthalocyanine except for the anionic iron phthalocyanine according to the mechanism shown in FIG. 31. More specifically, when the G-quadruplex is not present, these anionic phthalocyanines are associated with one another, and the UV absorption spectrum in such a state is as shown in FIG. 30 (A). However, when the G-quadruplex is mixed therewith, these anionic phthalocyanines intercalate in the G-quadruplex at least in part. Since thus intercalated anionic phthalocyanine is in the same state as those of the monomer, an absorbance peak at around 640 to 730 nm is found.

According to the present invention, the employed phthalocyanine unexpectedly exhibited such effects, despite the anionicity thereof, unlike the cationic anthraquinones and cationic porphyrins described above. In the mean time, such a large n-plane as in the G-quadruplex is not present in both the single stranded DNAs and double stranded DNAs, and further, electrostatic repulsion also occurs among the anionic substances. Consequently, any event is not caused even though they are mixed. Therefore, the present inventors discovered superior specificity for G-quadruplexes achieved by using an anionic phthalocyanine, contrary to common knowledges with respect to probes for detecting a DNA, which have been primarily believed that cationic probes are advantageous, and thus the present invention was accomplished.

Moreover, in regard to the coordination metal of phthalocyanine shown in FIG. 29, it is found that only the case in which iron was used can not detect the G-quadruplex for either the human telomeric DNA, or the G4T4G4 DNA. This would result from the reasons below. That is, typical structures of phthalocyanine include planar and shuttlecock type, generally referred to. The planar type has, as is clear from the naming, a plane shape as a whole of the molecule (FIG. 32 (A)). In contrast, the shuttlecock type has a structure in which a metal or a ligand thereof projects only in one direction from the phthalocyanine plane (FIG. 32 (B)).

The Iron (III) phthalocyanine-4,4',4'',4'''-tetrasulfonic acid, compound with oxygen monosodium salt hydrate used in Examples herein, which is an anionic iron phthalocyanine, has oxygen bound to the iron included as a coordination metal, belonging to the shuttlecock type phthalocyanines. In contrast, the other phthalocyanines used in Examples herein are all planar. As described above, the shuttlecock type phthalocyanine has a structure including projection from the mid region, thereby lacking in planarity. Therefore, contrary to the planar phthalocyanine capable of intercalating in the G-quadruplex according to the mechanism as shown in FIG. 31, the shuttlecock type phthalocyanine typified by the anionic iron phthalocyanine used in Examples herein cannot intercalate in the G-quadruplex due to lack of the planarity. As a result, the absorbance peak at around 640 to 730 nm is not found, which can be found in the case in which other anionic phthalocyanines were used. Such knowledges with respect to the interaction of the planar phthalocyanine and the shuttlecock type phthalocyanine for the G-quadruplex are found by the present inventors first in the world.

In summary, the present inventors ventured to use anionic phthalocyanine, contrary to conventional common knowledges, and discovered the difference in interaction of planar phthalocyanine and shuttlecock type phthalocyanine for G-quadruplexes first in the world. Accordingly, the method of the present invention for detecting a G-quadruplex with extremely high specificity using an anionic planar phthalocyanine was completed.

From the foregoing description, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the configuration and/or function of the present invention can be substantially altered without departing from the spirit thereof.

INDUSTRIAL APPLICABILITY

According to the present invention, the method for the specific detection of a G-quadruplex-forming DNA is useful as an analyzing process in the field of biotechnology.

[Reference Signs List]

| | |
|---|---|
| 1 | double DNA strands complementary to one another |
| 2 | T-A base pair |
| 3 | C-G base pair |
| 4 | G-quadruplex |
| 5 | G-quartet face |
| 6 | metal ion |
| 7 | chemical structure of G-quartet face |
| 8 | vessel |
| 9 | DNA strand other than G-quadruplex |
| 10 | probe bound to the G-quadruplex |
| 11 | free probe |
| 12 | putative G-quadruplex sequence |
| 13 | TS primer |
| 14 | elongated TS primer |
| 15 | primer for PCR |
| 16 | sample solution |
| 17 | solution including anionic phthalocyanine |
| 18 | solution including a single stranded DNA that serves as a substrate for telomerase |
| 19 | associated anionic phthalocyanine |
| 20 | monomer phthalocyanine |
| 21 | anionic phthalocyanine intercalated in G-quadruplex |
| 22 | planar phthalocyanine |
| 23 | shuttlecock type phthalocyanine |

The invention claimed is:

1. A method for determining an activity of telomerase contained in a sample solution, the method comprising steps of:
 (a) mixing the sample solution and a substrate solution to prepare a telomerase reaction solution, wherein the substrate solution contains an anionic DNA which serves as a substrate for telomerase;
 (b) maintaining the telomerase reaction solution under a condition to allow an anionic DNA addition reaction to be performed by telomerase;
 (c) mixing a solution containing an anionic planar phthalocyanine with a solution obtained following the step (b) to obtain a mixture;
 (d) measuring the absorbance at 640 to 740 nanometers of the mixture obtained in the step (c); and
 (e) determining the activity of telomerase on the basis of the absorbance obtained in the step (d).

2. The method according to claim 1, wherein the anionic planar phthalocyanine is either an anionic planar phthalocyanine in which at least one metal selected from the group consisting of copper, zinc, cobalt and nickel is coordinated, or an anionic planar phthalocyanine in which any metal is not coordinated.

3. The method for determining a telomerase activity according to claim 2, wherein the anionic planar phthalocyanine has at least one functional group selected from the group consisting of a carboxyl group, a metal salt of a carboxyl group, a sulfo group, and a metal salt of a sulfo group.

* * * * *

SEQUENCE LISTING

<160> NUMBER OF SEQ ID NOS: 6

<210> SEQ ID NO 1
<211> LENGTH: 6
<212> TYPE: DNA
<213> ORGANISM: Homo sapiens

<400> SEQUENCE: 1 ttaggg                                                              6

<210> SEQ ID NO 2
<211> LENGTH: 18
<212> TYPE: DNA
<213> ORGANISM: Homo sapiens

<400> SEQUENCE: 2
aatccgtcga gcagagtt                                                18

<210> SEQ ID NO 3
<211> LENGTH: 21
<212> TYPE: DNA
<213> ORGANISM: Homo sapiens

<400> SEQUENCE: 3
gggttagggt tagggttagg g                                            21

<210> SEQ ID NO 4
<211> LENGTH: 21
<212> TYPE: DNA
<213> ORGANISM: Homo sapiens

<400> SEQUENCE: 4
tttttttttt tttttttttt t                                            21

<210> SEQ ID NO 5
<211> LENGTH: 12
<212> TYPE: DNA
<213> ORGANISM: Homo sapiens

```
<400> SEQUENCE: 5
agaagagaaa ga                                                              12

<210> SEQ ID NO 6
<211> LENGTH: 11
<212> TYPE: DNA
<213> ORGANISM: Homo sapiens

<400> SEQUENCE: 6
ggggttttgg g                                                               11
```